United States Patent
DeHaven et al.

(10) Patent No.: US 10,573,406 B2
(45) Date of Patent: Feb. 25, 2020

(54) METHOD, APPARATUS AND COMPUTER PROGRAM PRODUCT FOR METABOLOMICS ANALYSIS

(71) Applicant: METABOLON, INC., Durham, NC (US)

(72) Inventors: Corey Donald DeHaven, Raleigh, NC (US); Robnet Thornhill Kerns, Durham, NC (US)

(73) Assignee: METABOLON, INC., Durham, NC (US)

( * ) Notice: Subject to any disclaimer, the term of this patent is extended or adjusted under 35 U.S.C. 154(b) by 500 days.

(21) Appl. No.: 14/856,184

(22) Filed: Sep. 16, 2015

(65) Prior Publication Data

US 2016/0019335 A1 Jan. 21, 2016

Related U.S. Application Data

(63) Continuation-in-part of application No. 13/800,010, filed on Mar. 13, 2013, now abandoned.
(Continued)

(51) Int. Cl.
*G16B 45/00* (2019.01)
*G16B 5/00* (2019.01)
*G16B 40/00* (2019.01)

(52) U.S. Cl.
CPC .............. *G16B 45/00* (2019.02); *G16B 5/00* (2019.02); *G16B 40/00* (2019.02)

(58) Field of Classification Search
None
See application file for complete search history.

(56) References Cited

U.S. PATENT DOCUMENTS

2003/0177143 A1  9/2003 Gardner
2005/0038608 A1  2/2005 Chandra et al.
(Continued)

OTHER PUBLICATIONS

Chagoyen, M. & Pazos, F. Tools for the functional interpretation of metabolomic experiments. Briefings in Bioinformatics 14, 737-744 (2013).*
(Continued)

*Primary Examiner* — Soren Harward
(74) *Attorney, Agent, or Firm* — Womble Bond Dickinson (US) LLP

(57) ABSTRACT

A method is provided for analyzing metabolite data in a sample, comprising analyzing a sample to determine a first number of metabolites, and amount of each metabolite, included in the sample, and a second number of the first number of metabolites that are regulated. Biochemical pathways are determined, each having a third number of the first number of metabolites that are included in the sample and in the determined biochemical pathway. For each of the determined biochemical pathways having the third number of metabolites, a fourth number of the second number of metabolites that are included in the sample and in the determined biochemical pathway that are regulated metabolites is determined. Each of the third number of metabolites within one of the determined biochemical pathways is displayed and distinguished by the amount of each corresponding metabolite included in the sample. An associated apparatus and computer program product are also provided.

21 Claims, 19 Drawing Sheets

Related U.S. Application Data

Figure 1:
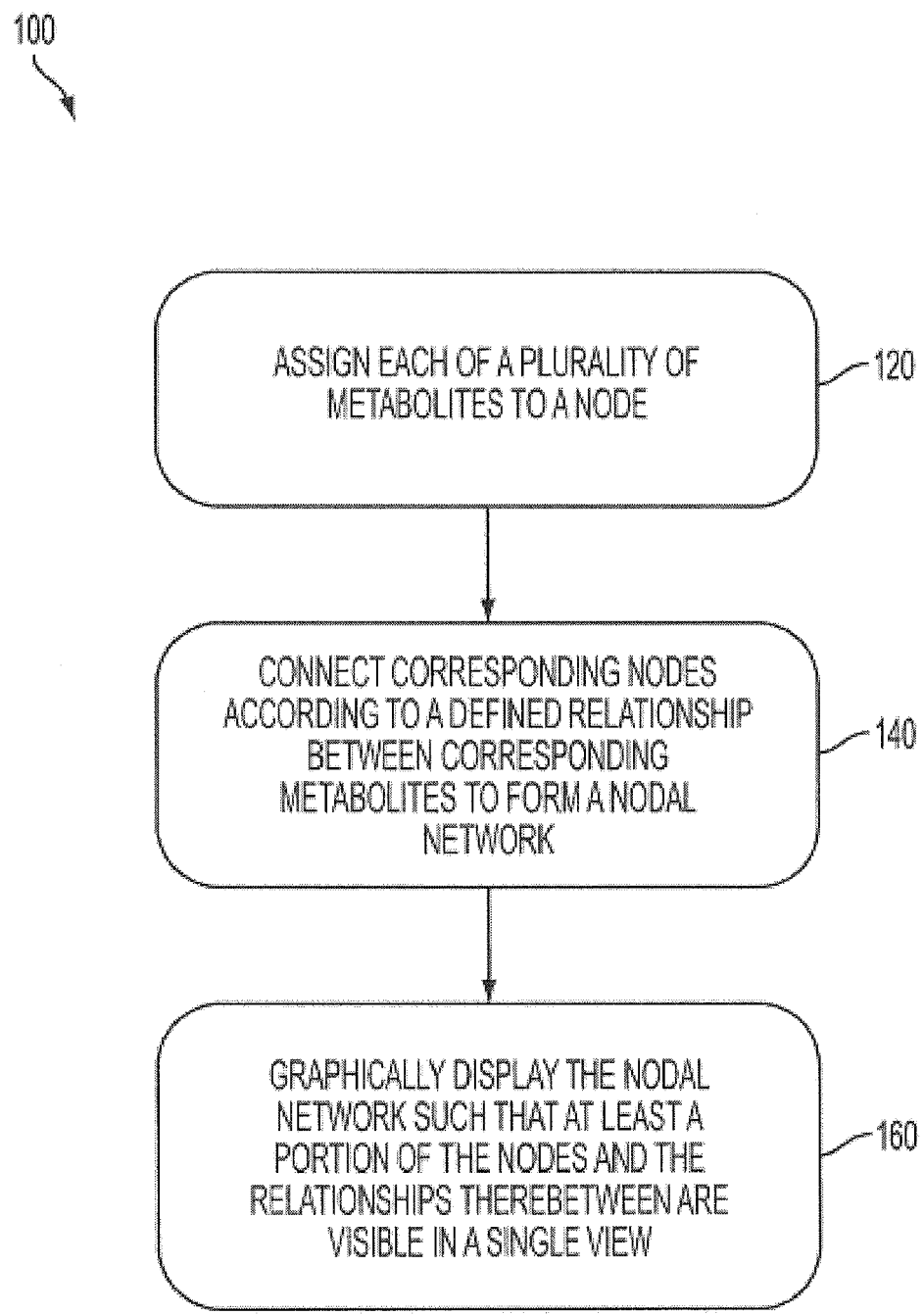

(60) Provisional application No. 61/752,758, filed on Jan. 15, 2013.

(56) References Cited

U.S. PATENT DOCUMENTS

| | | | |
|---|---|---|---|
| 2005/0076313 A1 | 4/2005 | Pegram et al. |
| 2005/0165594 A1 | 7/2005 | Chandra et al. |
| 2007/0219768 A1 | 9/2007 | Elkins et al. |
| 2007/0250299 A1 | 10/2007 | Paxson et al. |
| 2010/0262576 A1 | 10/2010 | Stockwell et al. |

OTHER PUBLICATIONS

De la Fuente, A. From 'differential expression' to 'differential networking'—identification of dysfunctional regulatory networks in diseases. Trends in Genetics 26, 326-333 (2010).*

Fukushima, A. DiffCorr: An R package to analyze and visualize differential correlations in biological networks. Gene 518, 209-214 (2013).*

Gehlenborg, N. et al. Visualization of omics data for systems biology. Nature Methods 7, S56-S68 (2010).*

Poisson, L. M., Sreekumar, A., Chinnaiyan, A. M. & Ghosh, D. Pathway-directed weighted testing procedures for the integrative analysis of gene expression and metabolomic data. Genomics 99, 265-274 (2012).*

Xia, J., Wishart, D. S. & Valencia, A. MetPA: A web-based metabolomics tool for pathway analysis and visualization. Bioinformatics 26, 2342-2344 (2010).*

Xia, J. & Wishart, D. S. Web-based inference of biological patterns, functions and pathways from metabolomic data using MetaboAnalyst. Nature Protocols 6, 743-760 (2011).*

Xia, J., Mandal, R., Sinelnikov, I. V., Broadhurst, D. & Wishart, D. S. MetaboAnalyst 2.0—A comprehensive server for metabolomic data analysis. Nucleic Acids Research 40, 127-133 (2012).*

Becker et al., "A Graph Layout Algorithm for Drawing Metabolic pathways", *Bioinformatics*, 2001, pp. 461-467, vol. 17.

Caspi et al., "The MetaCyc Database of metabolic pathways and enzymes and the BioCyc collection of Pathway/Genome Databases", *Nucleic Acids Research*, 2008, D623-631, vol. 36.

Karp et al., Pathway Tools Version 13.0: Integrated software for pathway/genome informatics and system biology, *Briefings in Bioinformatics*, 2010, pp. 40-79, vol. 11.

Lüdemann et al., Pathway Visualization and Editing System Bioinformatics, 2004, pp. 2841-2844, vol. 20.

Schreiber, F., "High Quality Visualization of Biochemical Pathways in BioPath." *In Silico Biology*, 2002, pp. 59-73, vol. 2.

Širava et al., "BioMiner-modeling, analyzing, and visualizing biochemical pathways and networks", *Bioinformatics* 2002, pp. S219-S230, vol. 18.

* cited by examiner

Biochemical Knowledgebase Summary Report

Project PROJ-CD-01BG
Analysis of chilled monkey brains

*This study attempts to gain a metabolic understanding of the differences in tastes of chilled monkey brains from south america and eastern asia at 4 times points.*

This study exhibits characteristics of:
  Liver Tox
  Hepatic Dysfunction
  DNA Damage
  Insulin Resistance 8 mammalian pathways are affected Out of 89 statistically significant metabolites, 40 are affected by the same enzyme The NAD+ => NADH + H+ reaction is involved in 72% of affected pathways There are 2 studies with similars changes to statistically significant metabolites:
  DFCI-05-11VW -- DFCI
  BIOG-02-11COP -- BIO There are 2 publications with similar changes to statistically significant metabolites:
  1. Setchell KD, Brown NM, Lydeking-Olsen E: The clinical importance of the metabolite equol-a clue to the effectiveness of soy and its isoflavones. J Nutr 2002, 132:3577-3584.
  2. Tolstikov VV, Flehn O: Analysis of highly polar compounds of plant origin: combination of hydrophilic interaction chromatography and electrospray ion trap mass spectrometry. Anal Biochem 2002, 301:298-307

There are 2 publications that reference the top 3 statistically significant metabolites:
  1. Setchell KD, Brown NM, Lydeking-Olsen E: The clinical importance of the metabolite equol-a clue to the effectiveness of soy and its isoflavones. J Nutr 2002, 132L3577-3584.
  2. Tolstikov VV, Flehn O: Analysis of highly polar compounds of plant origin: combination of hydrophilic interaction chromatography and electrospray ion trap mass spectrometry. Anal Biochem 2002, 301:298-307.

FIG. 6

| 3-hydroxy-3-methylglutarate(2-) (CHEBI:17325) | EMBL-EBI |
|---|---|
| Main  Automatic Xrefs | |

| | ChEBI Name | 3-hydroxy-3-methylglutarate(2-) |
|---|---|---|
| | ChEBI ID | CHEBI:17325 |
| | ChEBI ASCII Name | 3-hydroxy-3-methylglutarate(2-) |
| | DEFINITION | A dicarboxylic acid dianion that results from the removal of a proton from both of the carboxylic acid groups of 3-hydroxy-3-methylglutarate(2-) acid. |
| | Stars | ☆☆☆ This entity has been manually annotated by the ChEBI Team. |
| | Secondary ChEBI IDs | CHEBI: 11813, CHEBI: 20042 |

See structure as: ☑ Image ☐ Applet

📥 Download Molfile

- Find compounds which contain this structure
- Find compounds which resemble this structure more structures »

| Formula | Source |
|---|---|
| C6H8O5 | ChEBI |

| Net Charge | -2 |
|---|---|
| Average Mass | 160.12470 |
| InChI | InChI=1S/C6H10O5/c1-6(11,2-4(7)8)3-5(9)10/h11H2,2-3H2,1H3,(H,7,8)(H,9)/p-2 |
| InChIKey | InChIKey=NPOAOTPXWNWTSH-UHFFFAOYSA-L |
| SMILES | CC(O)(CC([O-])=O)CC([O-])=O |

ChEBI Ontology

Tree view

| | |
|---|---|
| Outgoing | 3-hydroxy-3-methylglutarate(2-) (CHEBI:17325) is a dicarboxylic acid dianion (CHEBI:28955) |
| | 3-hydroxy-3-methylglutarate(2-) (CHEBI:17325) has a functional parent glutarate(2-) (CHEBI:30921) |
| | 3-hydroxy-3-methylglutarate(2-) (CHEBI:30920) is a conjugate base of 3-hydroxy-3-methylglutarate(1-) (CHEBI:30920) |
| Incoming | 3-hydroxy-3-methylglutarate(1-) (CHEBI:17325) is a conjugate acid of 3-hydroxy-3-methylglutarate(2-) (CHEBI:17325) |

IUPAC Name
3-hydroxy-3-methylpentanedioate

| Database Links | Databases |
|---|---|
| C03761 | KEGG COMPOUND |
| CPD-547 | MetaCyc |

FIG. 9C

METHOD, APPARATUS AND COMPUTER PROGRAM PRODUCT FOR METABOLOMICS ANALYSIS

CROSS-REFERENCE TO RELATED APPLICATIONS

The present patent application is a continuation-in-part of U.S. patent application Ser. No. 13/800,010, filed Mar. 13, 2013, which claims priority to U.S. Provisional Patent Application No. 61/752,758; filed Jan. 15, 2013, the disclosures of which are incorporated herein by reference in their entirety.

BACKGROUND OF THE DISCLOSURE

Field of the Disclosure

Aspects of the present disclosure relate to metabolomics analysis and, more particularly, to a method, system, and computer program product for analyzing metabolomics data for a plurality of metabolites in a sample.

Description of Related Art

Sophisticated software systems have been developed for processing and analyzing metabolomic datasets. One exemplary system may comprise, for example, core LIMS functionality (sample tracking, management), instrument integration, automated data processing, visualization/reporting tools, data quality/review tools, and statistical analysis functionality. One positive aspect of running studies of consistently high-quality in high-throughput, is that an enormous knowledgebase is formed over time. Metabolites in the library, both known and unknown, that are identified in the studies are associated, for example, with pathways, public id's, physical properties, sample metadata, matrix types, etc. and also contain statistical data in the context of the study. This means that for any particular metabolite, there may be many studies in which that metabolite, for example, was identified, involving multiple pathways, disease states or other associated metadata. This knowledge and accumulated information may be extremely valuable in biomarker discovery, mechanism identification, optimization or other questions pertaining to metabolite function. In this regard, software and hardware systems are readily scalable for sample processing capacity and readily refined for improving data quality.

However, there still exists a bottleneck with respect to this wealth of information, in terms of biochemical interpretation. That is, it may not necessarily be realistic to provide significant automation to the process of metabolite analysis result interpretation, but, lacking such automation, there are significantly limited mechanisms for leveraging this wealth of past knowledge.

There also exist relatively simple pathway associations for metabolites, limited, for example, to super-pathways (e.g., carbohydrate pathways) and sub-pathways (e.g., pyrimidine degradation pathways). However, complex hierarchical associations such as, for example, inter- and intra-pathway relationships, though desirable, may be lacking in the state-of-the-art. This may result, for example, in deficiencies in performing complex biochemical pathway analysis, such as enrichment analysis, and deficiencies in visualizing those identified relationships.

One other deficiency of current available systems is that, for example, since there is no easily accessible storage mechanism for relating metadata, statistics, and pathways, the wealth of metabolite data may not be easily shared and understood by collaborators.

SUMMARY OF THE DISCLOSURE

The above and other needs are met by aspects of the present disclosure, wherein one such aspect relates to a method of analyzing metabolomics data for a plurality of metabolites in a sample. Such a method comprises analyzing a sample to determine a first number of metabolites, and the amount of each metabolite, included in the sample, as well as a second number of metabolites, corresponding to an amount of the first number of metabolites included in the sample that are regulated metabolites. One or more biochemical pathways each having a third number of metabolites, corresponding to an amount of the first number of metabolites determined to be included in the sample and in the determined biochemical pathway is determined. For each of the determined biochemical pathways having the third number of metabolites, a fourth number of metabolites, corresponding to an amount of the second number of metabolites determined to be included in the sample and in the determined biochemical pathway that are regulated metabolites is determined. For one of the determined biochemical pathways, each of the third number of metabolites within the one of the determined biochemical pathways is displayed, distinguished within the display by the amount of each corresponding metabolite determined to be included in the sample.

In another aspect of the present disclosure, an apparatus comprising processing circuitry is provided. The processing circuitry of this example embodiment may be configured to control the apparatus to at least perform the steps of the method aspect.

In yet another aspect of the present disclosure, a computer program product is provided comprising at least one non-transitory computer readable storage medium having computer program code stored thereon. The program code of this embodiment may include program code for at least performing the steps of the method aspect upon execution thereof.

Aspects of the present disclosure thus address the identified needs and provide other advantages as otherwise detailed herein. It will be appreciated that the above summary is provided merely for purposes of summarizing some example embodiments so as to provide a basic understanding of some aspects of the disclosure. As such, it will be appreciated that the above described example embodiments are merely examples and should not be construed to narrow the scope or spirit of the disclosure in any way. It will be appreciated that the scope of the disclosure encompasses many potential embodiments, some of which will be further described below, in addition to those here summarized.

BRIEF DESCRIPTION OF THE SEVERAL VIEWS OF THE DRAWING(S)

Figure 12:
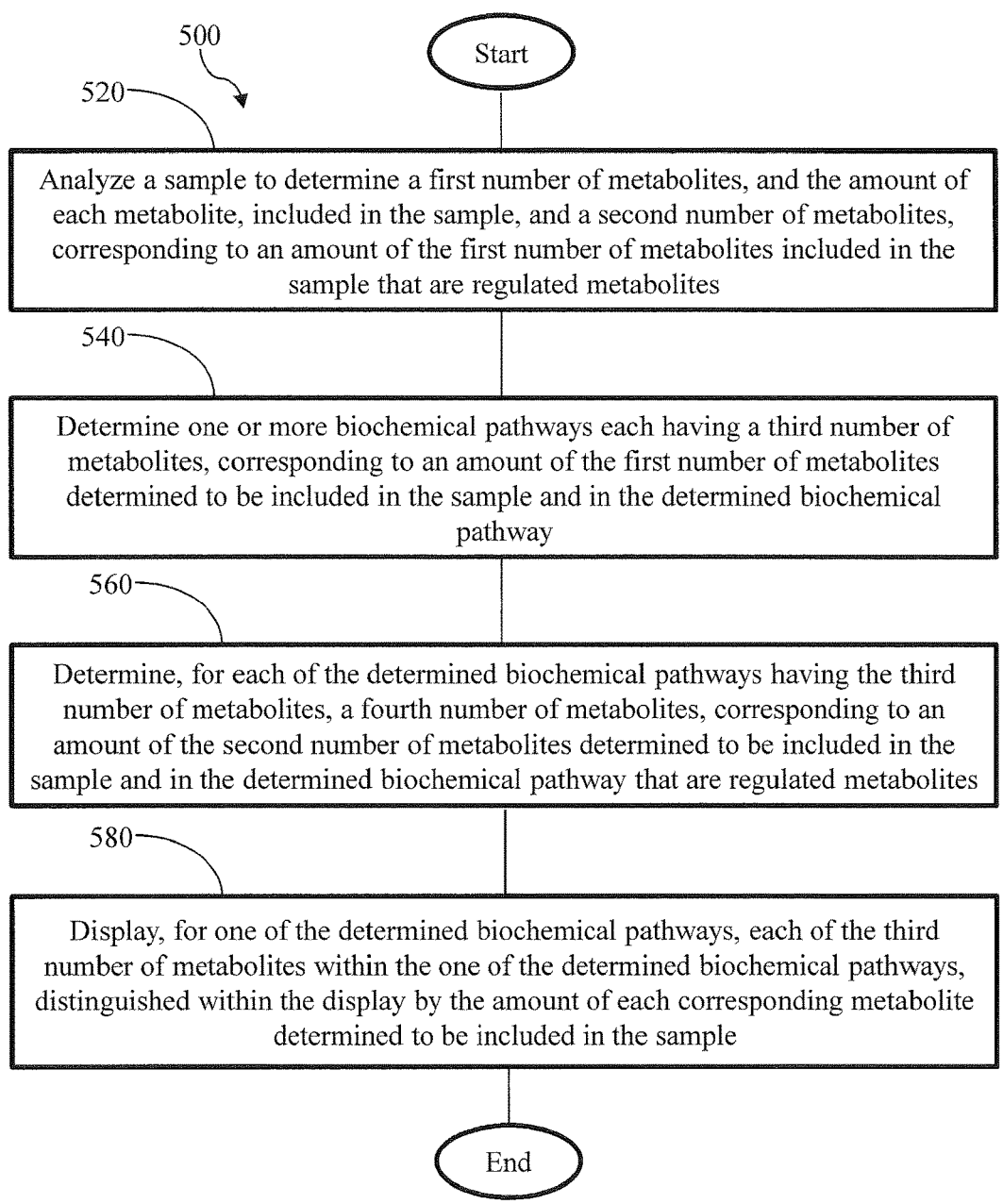
Figure 13:
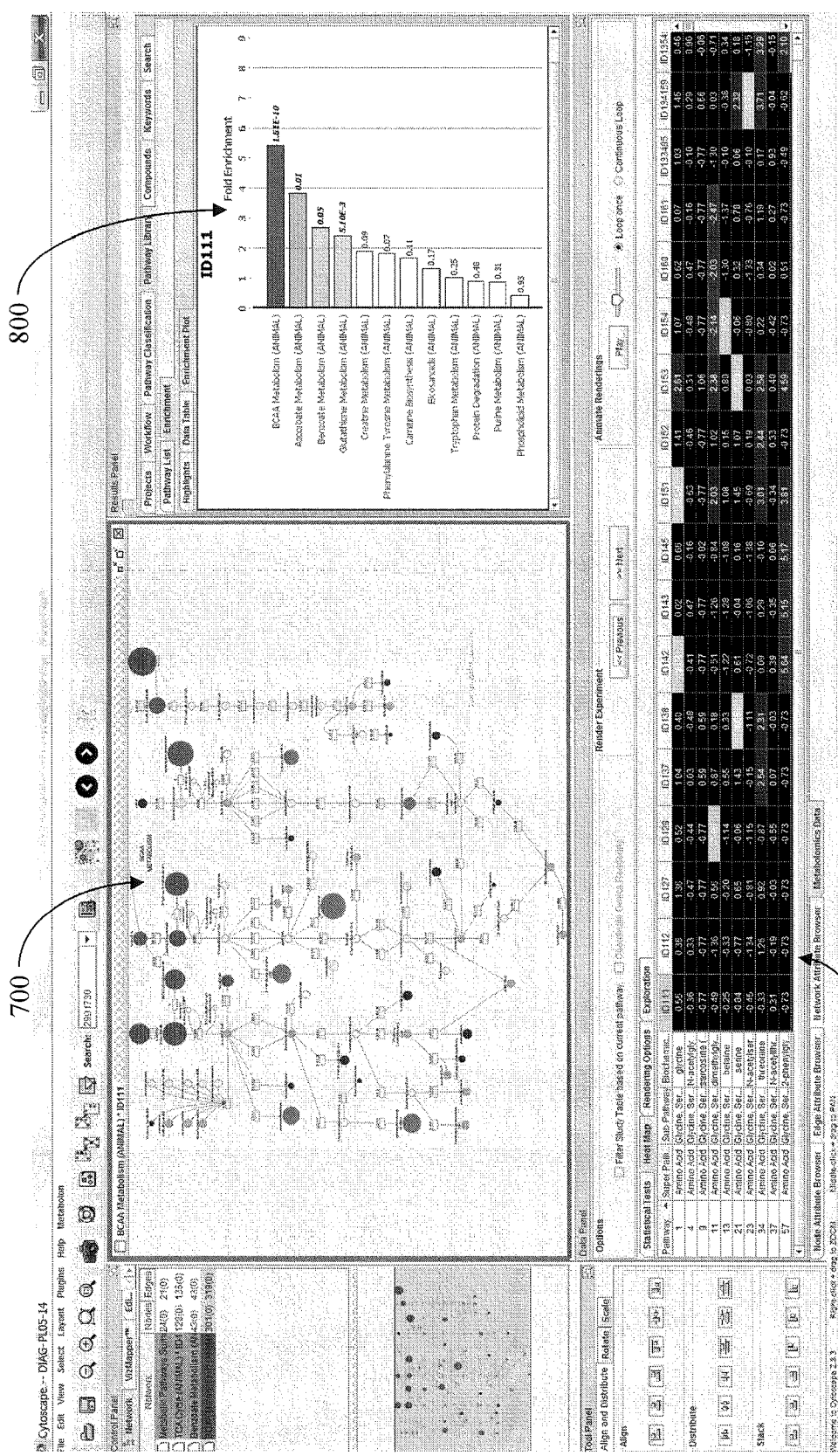
Figure 14:
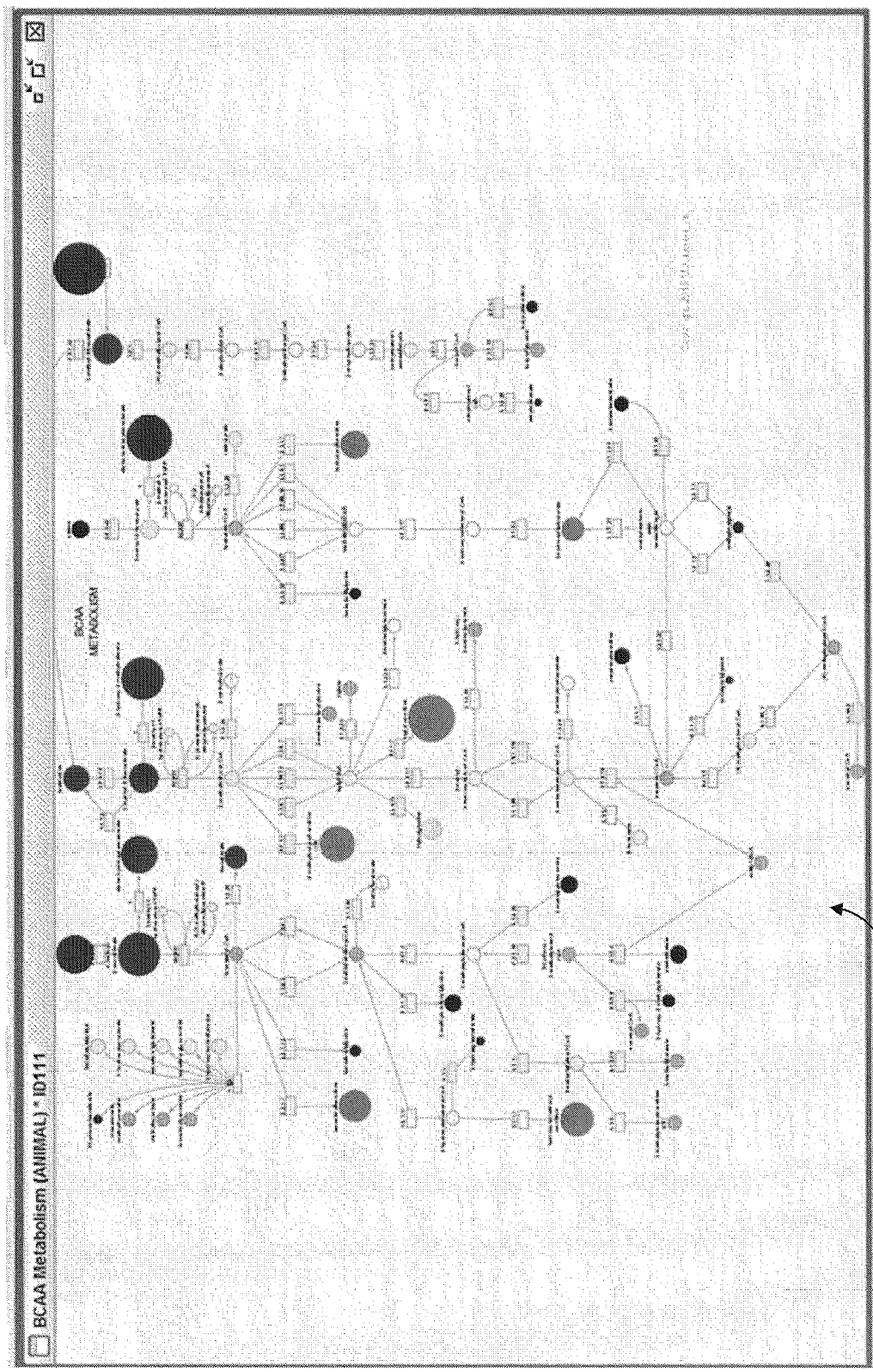
Figure 15:
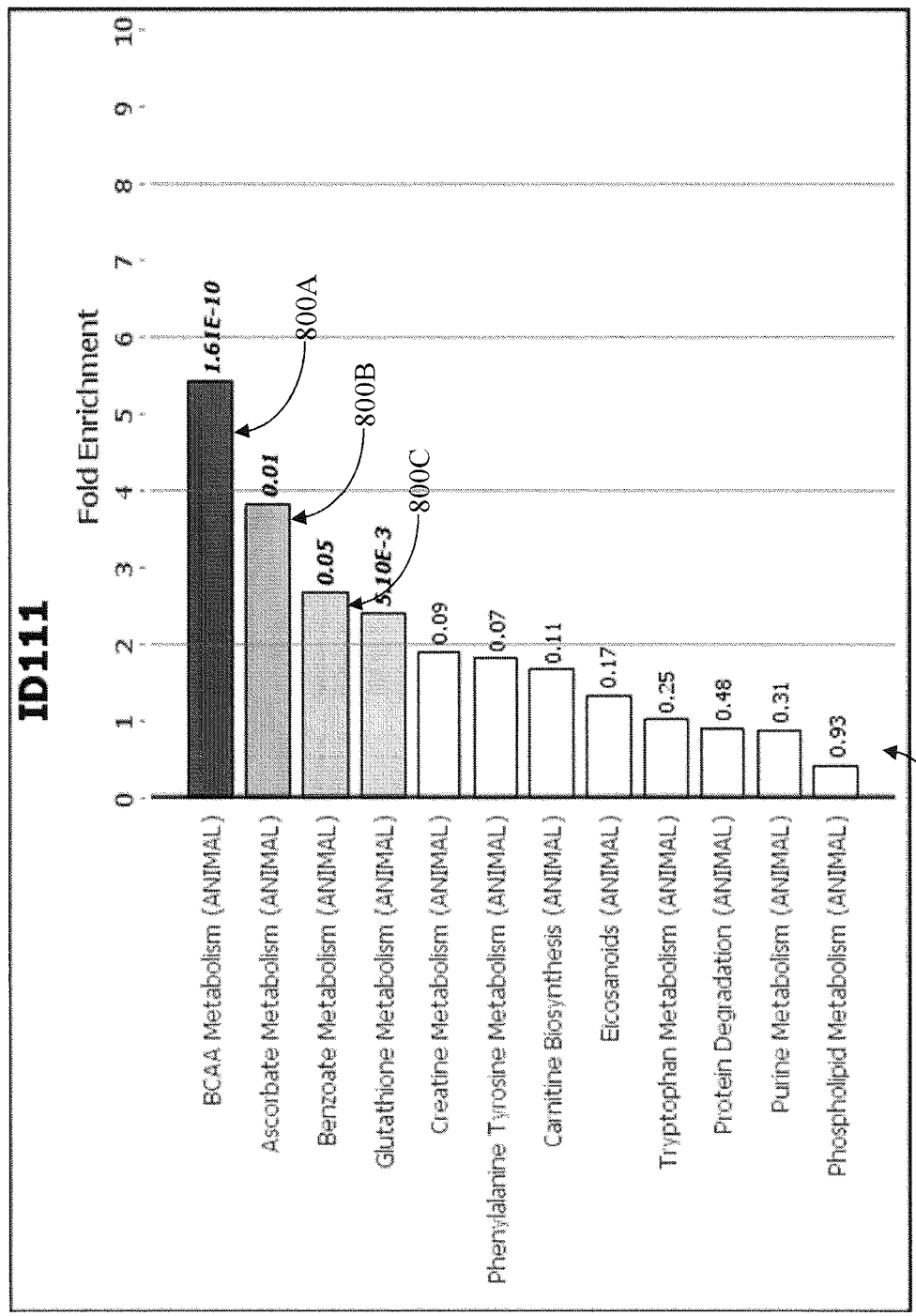
Figure 16:
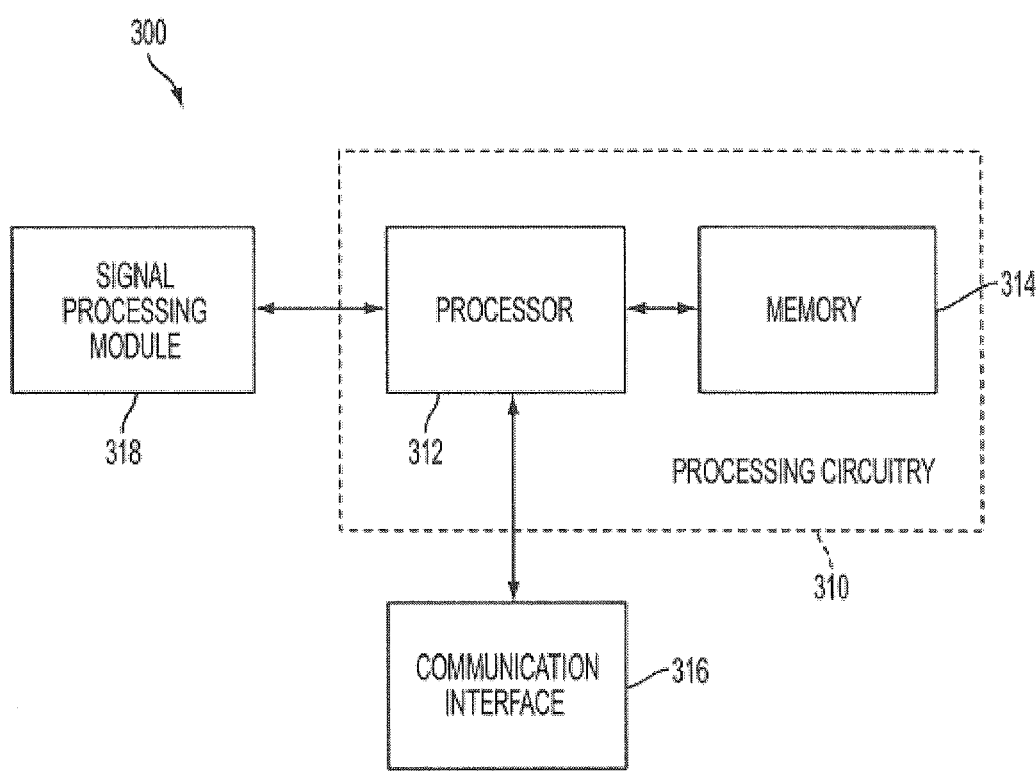

Having thus described the disclosure in general terms, reference will now be made to the accompanying drawings, which are not necessarily drawn to scale, and wherein:

FIG. 1 schematically illustrates a method of analyzing metabolomics data for a plurality of metabolites, according to one aspect of the present disclosure;

FIGS. 2-6, 7A, 7B, 8, 9A-9C, 10 and 11 schematically illustrate various aspects of a method, system, and computer program product, according to the present disclosure;

FIG. 12 schematically illustrates a method of analyzing metabolomics data for a plurality of metabolites in a sample, according to another aspect of the present disclosure;

FIGS. 13-15 schematically illustrate various aspects of a method, system, and computer program product, associated with FIG. 12 and other aspects of the present disclosure; and FIG. 16 schematically illustrates an apparatus configured to implement a method of analyzing metabolomics data for a plurality of metabolites, according to one aspect of the present disclosure.

DETAILED DESCRIPTION OF THE DISCLOSURE

The present disclosure now will be described more fully hereinafter with reference to the accompanying drawings, in which some, but not all aspects of the disclosure are shown. Indeed, the disclosure may be embodied in many different forms and should not be construed as limited to the aspects set forth herein; rather, these aspects are provided so that this disclosure will satisfy applicable legal requirements. Like numbers refer to like elements throughout.

In one aspect, the present disclosure is directed to implementing a system that provides storage, query-tools, and visualization of a biochemical knowledgebase. Such a system may store extensive and, in some instances, complete, biochemical pathway information including, for example, biochemicals, reactants, products, cofactors, directionality, intra-pathway relationships, combinations thereof, and/or any other suitable relationships or associations related to the biochemical pathway information. With such capabilities, aspects of the present disclosure may provide, for example, integration of study data within internal and external ontologies and public data sources, and may also provide advanced query and visualization tools for similarity analysis. That is, in one aspect of the present disclosure, a method 100 is provided (FIG. 1) for analyzing metabolomics data for a plurality of metabolites. Each metabolite is assigned to a node (Block 120). Associated nodes are connected according to a defined relationship between corresponding metabolites to form a nodal network (Block 140). The nodal network is visually/graphically displayed such that at least a portion of the nodes and the relationships therebetween are visible in a single view (Block 160). In some instances, at least one of the nodes and one of the relationships is annotated with at least one of empirical information associated therewith and relational information associated with other nodes and relationships.

In various aspects, the nodal network may be searched according to at least one attribute or search characteristic of one of the metabolites, the nodes, the relationships, and the annotations. Such a search characteristic may be, for example, a key word or a chemical formula or structure. The results of the search may be graphically displayed in relation to the nodal network. In some instances, visually/graphically displaying the nodal network further comprises visually/graphically displaying the nodal network such that associated nodes are disposed in visual proximity to each other such that relationships associated with each node are visually distinctive. In addition, an indicium of a relationship between associated nodes can be associated with the respective associated nodes in the nodal network. The indicia of the relationship between associated nodes may be visually/graphically displayed in visual proximity to the associated nodes of the nodal network. In some instances, a relational database can be formed, including the nodes, the metabolites assigned thereto, and the defined relationships between corresponding metabolites. Further, the relational database may be visually displayed in visual proximity to the nodal network. In other instances, the relational database can be visually displayed in a single view separately from the nodal network and toggling the single view between the relational database and the nodal network on demand. In yet other instances, at least a portion of one of the metabolites, the nodes, the relationships, and the annotations, may be associated with a link to external information associated therewith, and retrieving the external information in response to selection of the link.

As previously discussed, a software system for the processing and analysis of metabolomic datasets (FIG. 2) may comprise, for example, core LIMS functionality (i.e., sample tracking, management), instrument integration, automated data processing, visualization/reporting tools, data quality/review tools, and statistical analysis functionality. The integration of the distinct software modules required to process and analyze metabolomic studies, and the centralization of such data, allows the process to be pipelined regardless of the study design or number of sample being processed. Such pipelining of the process may be beneficial, for example, in that sample throughput may be enhanced by automated sample and data processing with tools allowing for batch data QC processing. As such, analysis instruments can be utilized to run at specified operational capacity. In other instances, study capacity may be improved since automated sample and data processing may also enable extremely high reproducibility, which allows for high sample numbers within particular studies. Data quality may also be improved by intelligent data processing, result visualization, and QC tools that leverage the batch-oriented nature of the process result in only high-quality data being fed into statistical analysis. Further, improved reproducibility may result from automated data processing, limited human interaction with the data until the visual QC steps, and stable instrumentation. In addition, enhanced scalability may result. Such studies may also increase and capture the value of historical knowledge. That is, since one benefit of running design-independent studies, of consistently high-quality in high-throughput, is that a significant knowledge base may be formed over time in a library. Metabolites in a library, both known and unknown, that are identified in these studies are associated with certain "metabolite metadata" such as, for example, pathways, public id's, physical properties, sample metadata, matrix types, etc. and also contain statistical data in the context of the study. As such, for any particular metabolite, there may be many studies in which that metabolite was identified and discovered to involve multiple pathways, disease states or other associated metadata. This extensive knowledge may be particularly valuable, for example, in biomarker discovery, mechanism, optimization or other questions pertaining to function. Further, one skilled in the art will appreciate that, though reference is made herein to aspects of the method, system, and computer program product being particularly directed to metabolites and metabolomic systems, such reference is for exemplary purposes only. That is, one skilled in the art will appreciate that aspects of the method, system, and computer program product disclosed herein may be similarly and readily applicable to any biologic data accumulated in an extensive knowledgebase (i.e., generally any "-omics" data such as, for example, transcriptomics, proteomics, DNA copy number, etc.). As such, the examples presented herein involving metabolites/metabolomic systems are not intended to be limiting to the applicability of such aspects of the methods, systems, and computer program products herein in any manner.

In some aspects, the present disclosure is directed to determining a biological meaning, definition, relationship, or the like for metabolite data sets, using assets such as, for example, study context available through study design information, matrix parameters, and sample metadata. In addition, such data sets may include lists of statistically significant metabolites with associated statistical values and public identifiers, and/or data from other studies (including, for instance, associated design information, sample types, metadata, statistics, metabolites, etc.). In determining a biological interpretation, it may be helpful, for a group of statistically significant metabolites, to determine, for example, common pathways that may be affected; internal historical experience (i.e., metabolites up- or down-regulated), external historical experience (i.e., publications); any changes for a given drug (i.e., changes in metabolite across data sets); any other groups of metabolites that may be affected by the same enzymes; any pathways that may be affected by varying NAD levels; any correlation of low NAD levels to a list of pathways; and/or other relationships. In making some of these determinations, some required information may include, for example, a list of affected pathways; knowledge of common reactions and/or enzymes of affected pathways; and results of public literature searches based on a particular list of metabolites.

Figure 3:
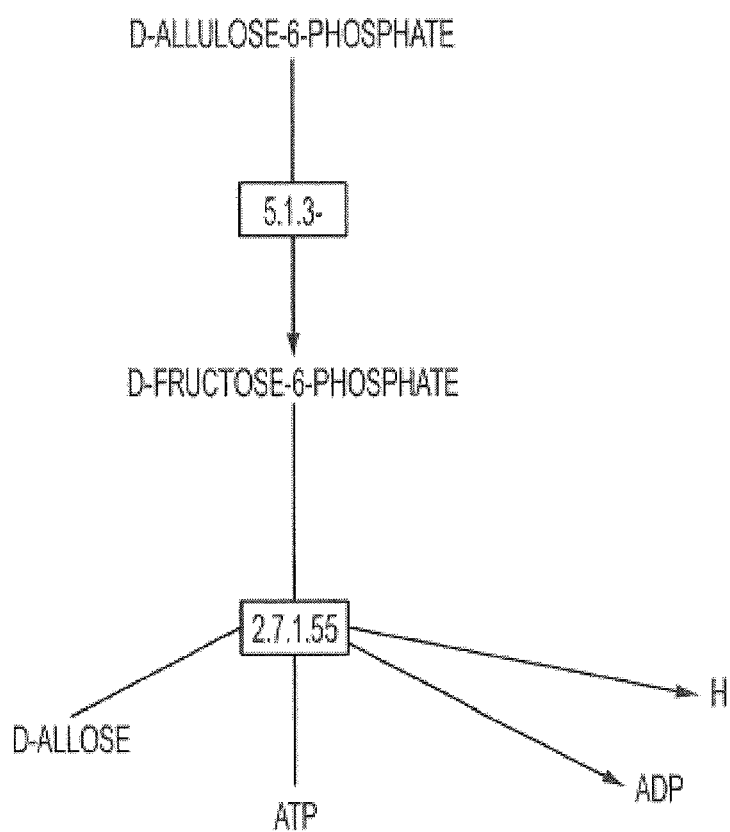
Figure 4:
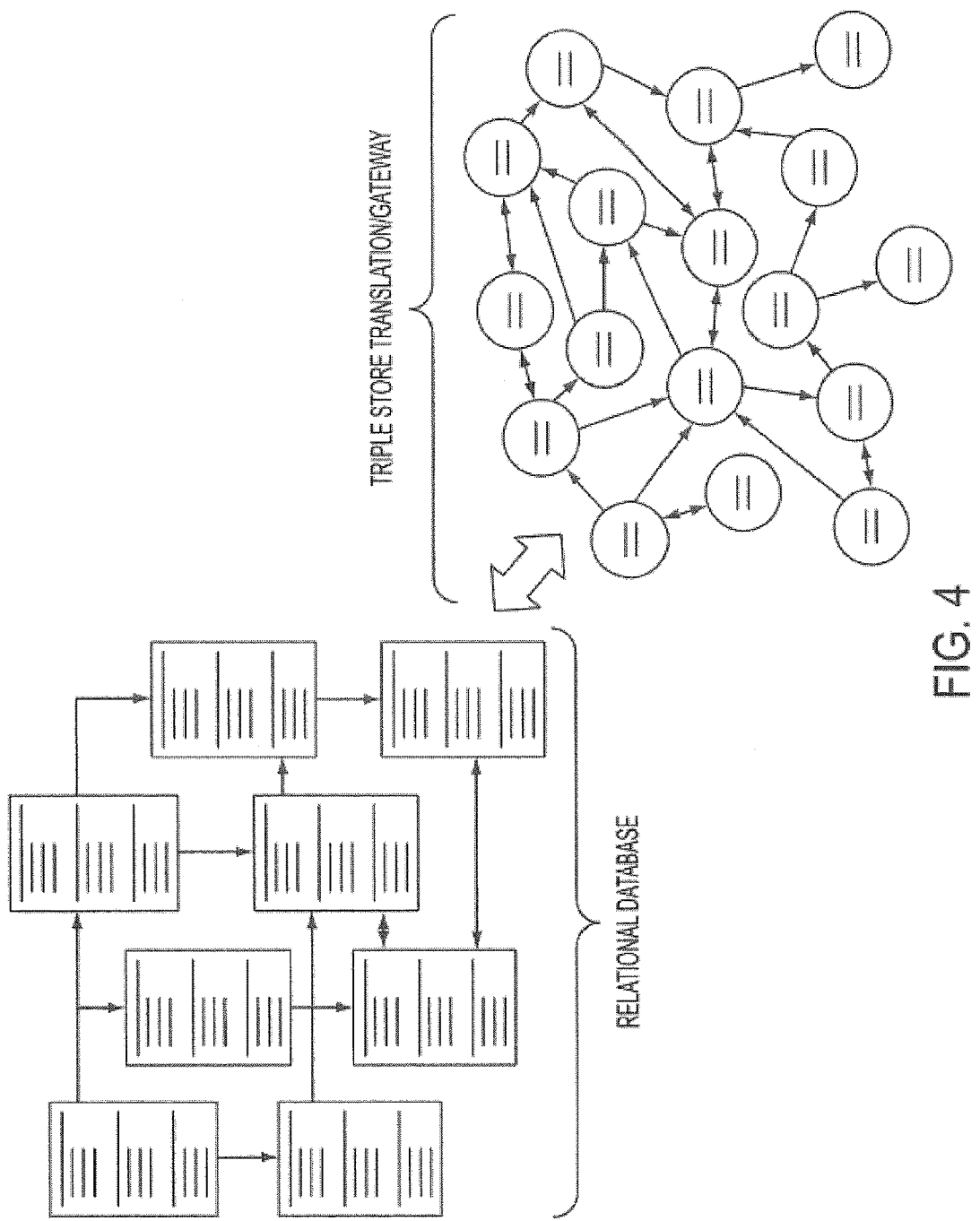

An initial aspect of the functionality of systems, methods, and computer program products of the present disclosure includes defining an initial framework, including particular nodes and relationships, for example, from an internal knowledge base of metabolites and discovered characteristics from particular studies (FIG. 3). In one example, metabolites and/or enzymes may be assigned to nodes, and the reaction side may be assigned to edges. In one aspect, each node may be annotated with one or more attributes. The attributes are associated with the node and are stored in a database. In some instances, one or more attributes may be uploaded to the database for each metabolite data set. In one example, nodes may be assigned one or more attributes related to metabolomics data and, optionally, may be assigned one or more attributes related to additional types of -omics data (e.g., genomics, transcriptomics, proteomics, DNA copy number, etc.). In this regard, particular aspects may include, for example, a relational database to triple store translation/gateway functionality (see, e.g., FIG. 4) with toggling therebetween. That is, in some instances, a translator may be required to translate the internal metabolite data stored in a particular relational schema and into a triple store (i.e., a graphic). This transition of internal metabolite study data to the triple store may be a selective or gated process controlled, for example, by a project director. As such, one skilled in the art will appreciate that not all internal metabolite studies will necessarily be converted. The converted categories may include relational objects or parameters, such as, for example, client name/ID; project name/ID; sample set (study) name/ID; organism; species; matrix; matrix type; sample metadata [name/value pair]; metabolites; statistical values [name/value pair]; pathway; public identifiers; and/or combinations thereof (FIG. 4).

In another aspect, such functionality may include, for example, an editing tool configured to edit, for example, ontology values, network associations/relationships, etc. More particularly, such an editing tool may be configured to add ontology values or structures not contained in the relational schema and/or to create relationships across objects and/or to external ontology sources.

Figure 5:
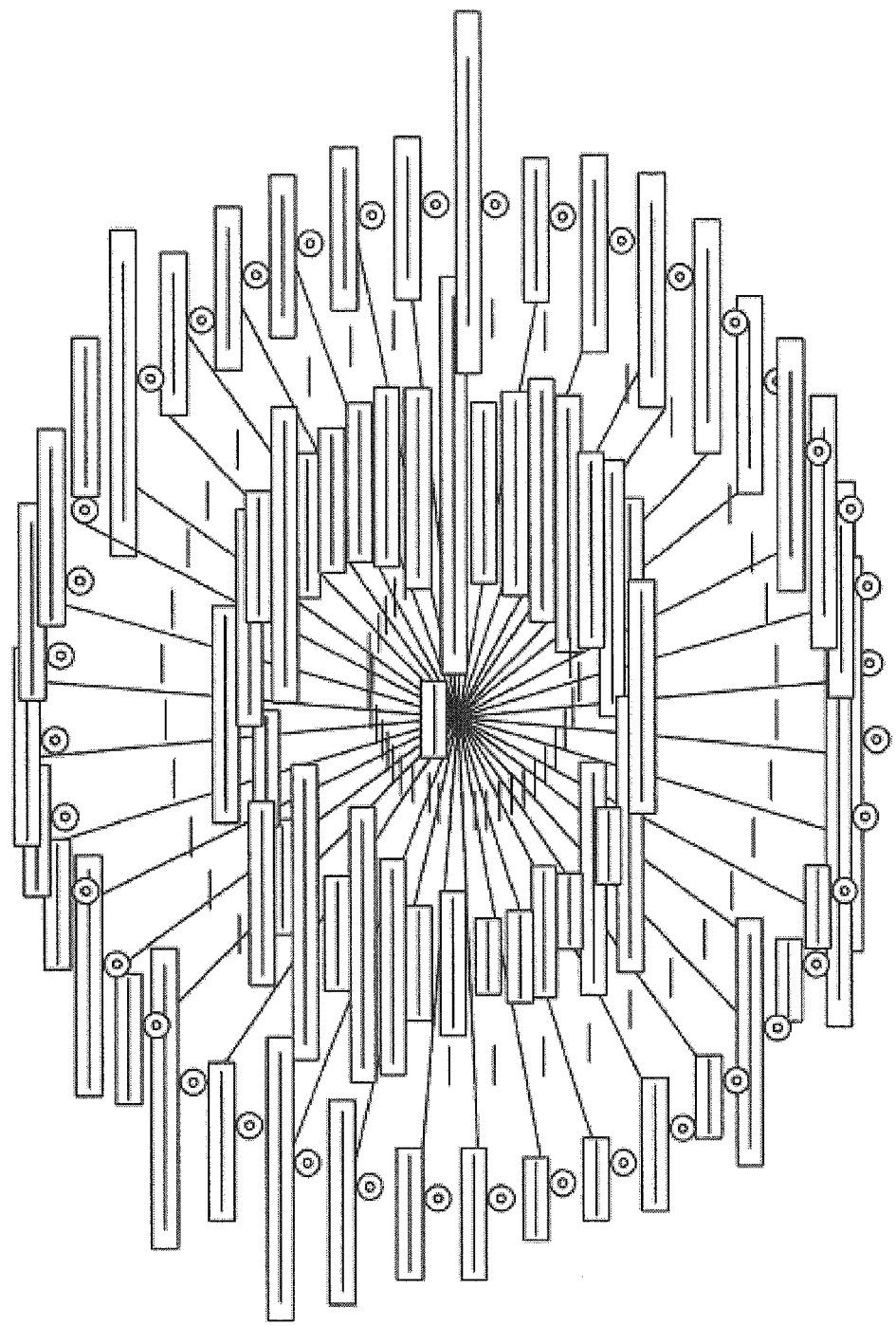

Yet another aspect involves a manipulation engine or tool configured to allow a user to run queries on the metabolite data and/or provide visualization of that data. More particularly, such a manipulation engine or tool may be configured to perform predetermined or custom queries of the triple store, and allow the user to visualize and/or report on the results (i.e., visualize results in a graphical environment or as a graphic depicting relevant nodes and relationships therebetween). In some instances, the manipulation engine/tool may also be configured to include a back-end engine or component for conducting multiple advanced queries to determine, for example, historical and/or public relationships, wherein the results of these advanced queries may also be graphically displayed and otherwise manipulated, for example, by an mLIMS application (i.e., a theme generator) (FIG. 5).

In some instances, the manipulation engine/tool may be configured to analyze the metabolite data to identify characteristics indicating predetermined analysis situations (i.e., a theme generator for identifying themes) (FIG. 6). In such situations, for example, the results of an analysis may result in a web-page being presented to the user with answers (or indicators) in response to the query which may include links to various tools corresponding to the nature of the results and/or original query. Aspects directed to the mLIMS integration and visualization features may, in some instances, require access to the triple store via web service methods. In some instances, particular components such as reports, the theme generator, and/or the actuation of the analysis itself may be launched from the mLIMS application or may utilize data retrieved by web services, wherein such functionality may be integrated directly into the mLIMS application framework or may be run or executed externally thereto.

In other aspects, the systems, methods, and computer program products of the present disclosure may require, for example, identification of the various semantic schemas (i.e., ontologies) applicable to an existing data library; implementation of an appropriate storage mechanism for the knowledge base utilizing the identified schemas integrated with an existing relational database; query functionality/visualization/reporting of the data within the knowledge base; and exporting of that data in standard formats. In addition to storing the biochemical knowledge base, and building a network of chemical pathways/relationships/associations in diverse functional areas such as, for example, disease, matrix, observation, clinical value, etc., tools may be implemented for editing, searching, and providing visualization network data for associated users.

Figure 2:
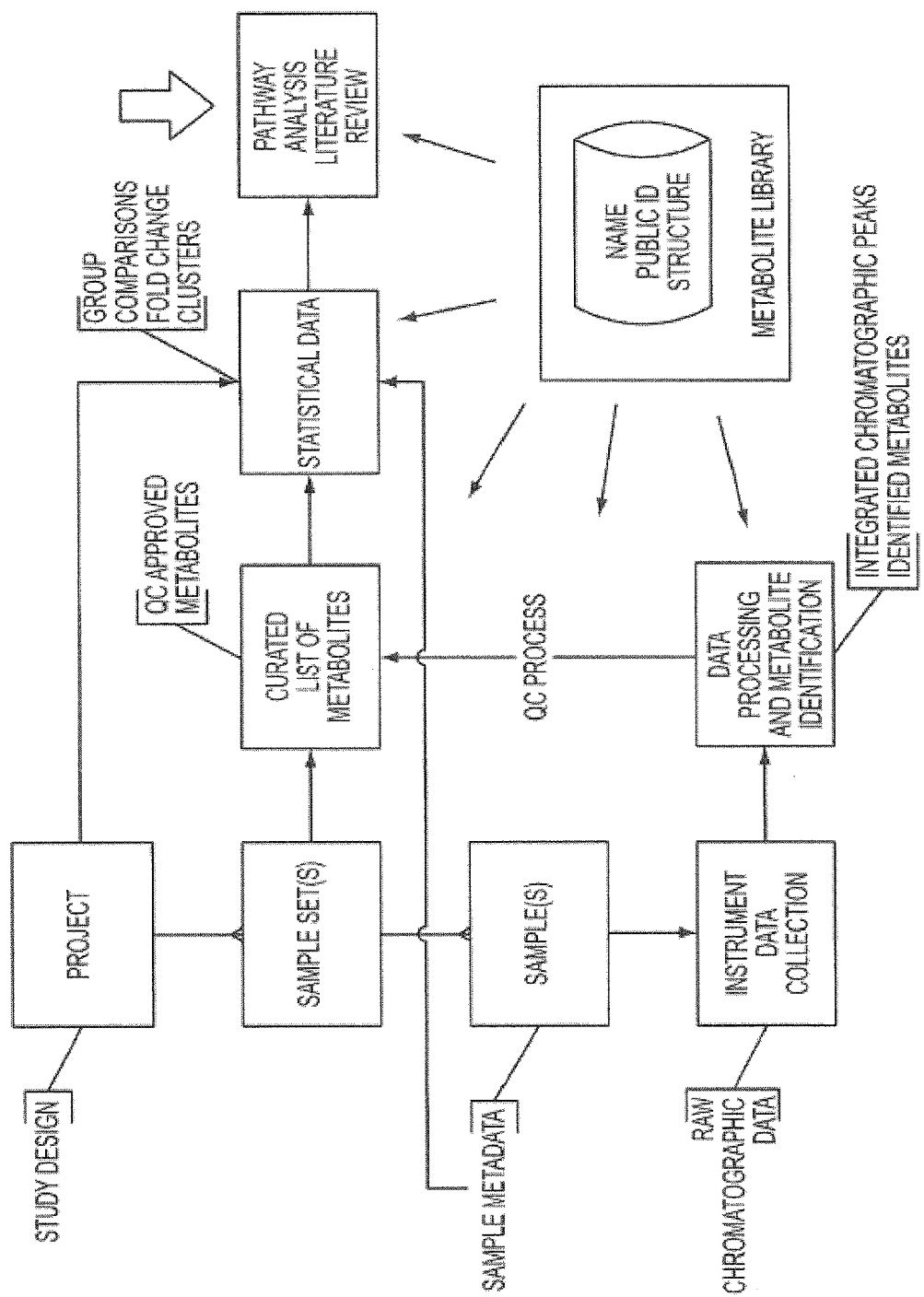
Figure 7A:
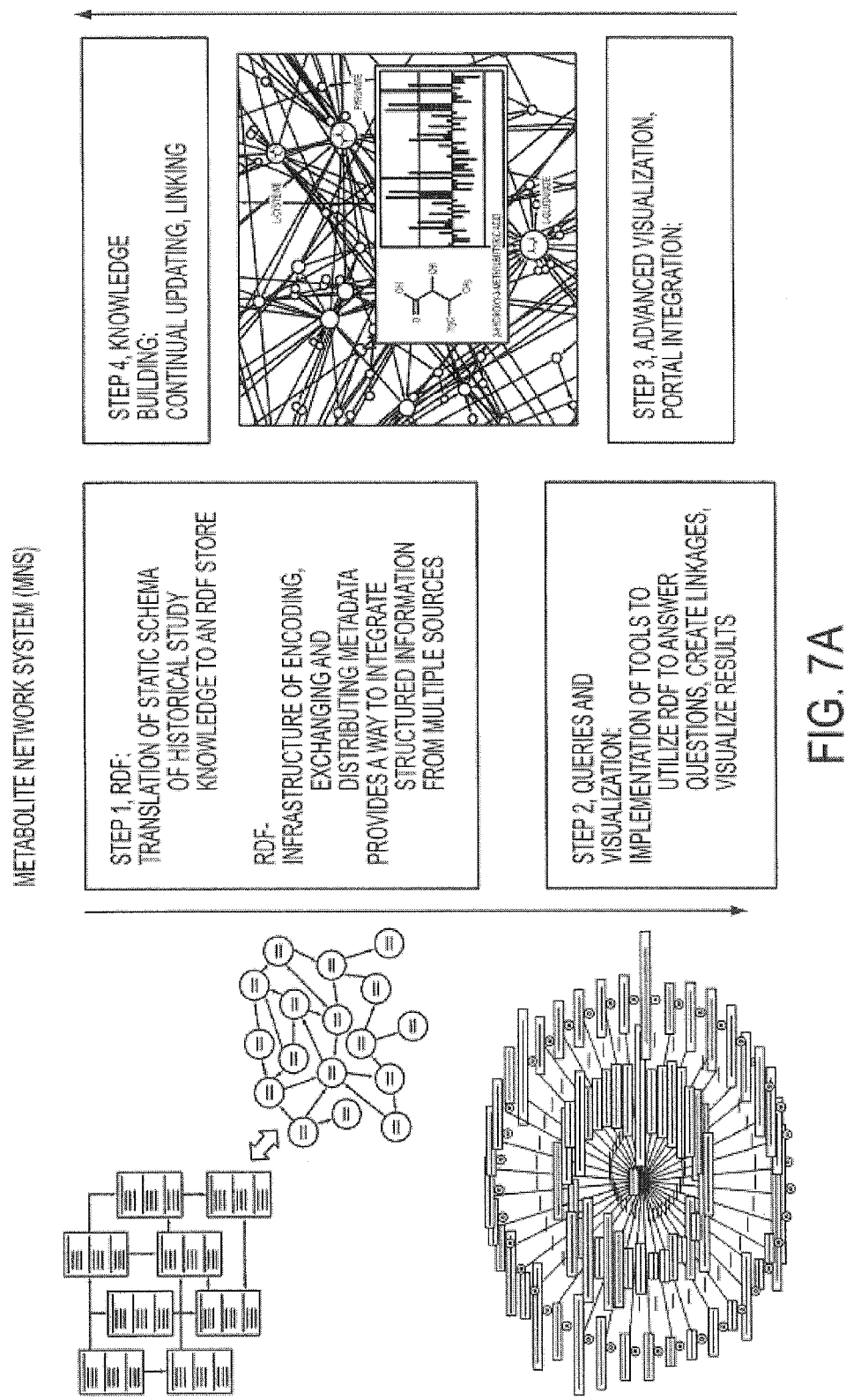
Figure 7B:
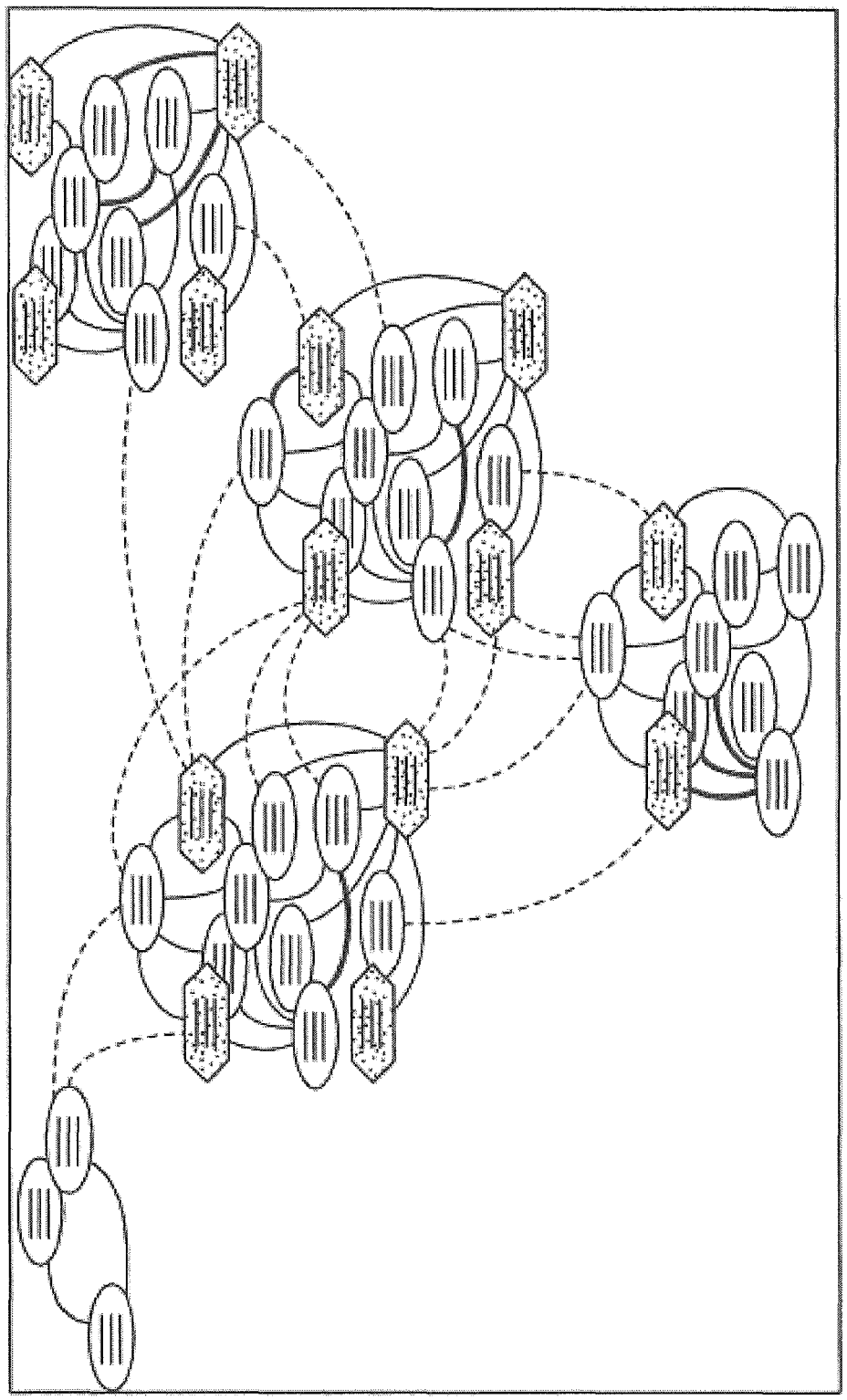

One skilled in the art will appreciate that there may exist certain desktop-based, modular, open-source platforms for network visualization and analysis (e.g., see FIG. 2). As such, particular "plugins" may be developed to provide additional functionality to the platform for particular data architectures and analysis schemes for certain networks. As such, aspects of the systems, methods, and computer program products of the present disclosure may be implemented, configured, associated with, and/or realized as a plugin for such platforms, which may particularly allow visualization of large networks (i.e., metabolite nodal networks, as disclosed herein, or at least a portion thereof, in a single view), as well as research and analysis associated therewith. Graphic visualization features are customizable from providing various types of graphs (e.g., cyclic, directed, tree, etc.) to the annotation of individual nodes and/or pathways/relationships/associations. In some aspects, users can map several images, annotations, or the like for each node and, having the ability to navigate through the nodal network, may readily be able to visualize large scale networks such as, for instance, the human interactome. In some aspects, various types of charts may be mapped to the nodes, as a custom graphics function. In other instances, the user may have the capability to browse chemical structures of metabolites in a specific user panel or directly in the relevant nodes (FIGS. 7A and 7B).

Figure 8:
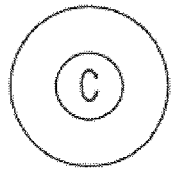

In other aspects, the systems, methods, and computer program products of the present disclosure may be configured as a web service client, for example, by directly connecting to external databases, and importing network data and annotation data. Several public databases may be available for download via specific queries (FIG. 8). Graphics-based analysis tools, such as node clustering and filtering, may also extend the functionality disclosed herein. Additional cheminformatics software tools can also be used by the plugin configuration via external program piping, as necessary or desired, wherein such tools can be integrated to provide or otherwise be incorporated into a user-friendly (graphical) interface.

In particular aspects, efficient loading and mapping of the structured metabolite ontology may be implemented synergistically with other chemical/biological data available from other sources such as, for example, the public domain. Appropriately structured and accessible data storage may facilitate efficient loading of large amounts of data, as involved, for example, with chemical and biological data in metabolomic analysis. In this regard, certain systems, such as a text-based data management system, may allow rapid communication between aspects of the systems, methods, and computer program products of the present disclosure, and the metabolomics database, and may include necessary information, such as metabolite name, chemical structure, internal and external ids, and/or will allow any necessary data to be retrieved as necessary. Files may be encrypted, as necessary, and depending on the user's privileges, certain parts of the information could be hidden on the front-end desktop application. In turn, the metabolomics database may be enhanced by associating, with each metabolite, other public database identifiers that may be available, such as PubChem_id, Chemspider_id, Gene_id, ChEBI_id, STITCH_id, CTD_id, and PDB_id. Associating metabolites with public data entries may facilitate the retrieval of diverse information spread across multiple public data sources, particularly online data sources, wherein automatic search of such identifiers may be facilitated by different cheminformatics software tools.

Figure 9A:
Figure 9B:
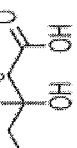
Figure 10:
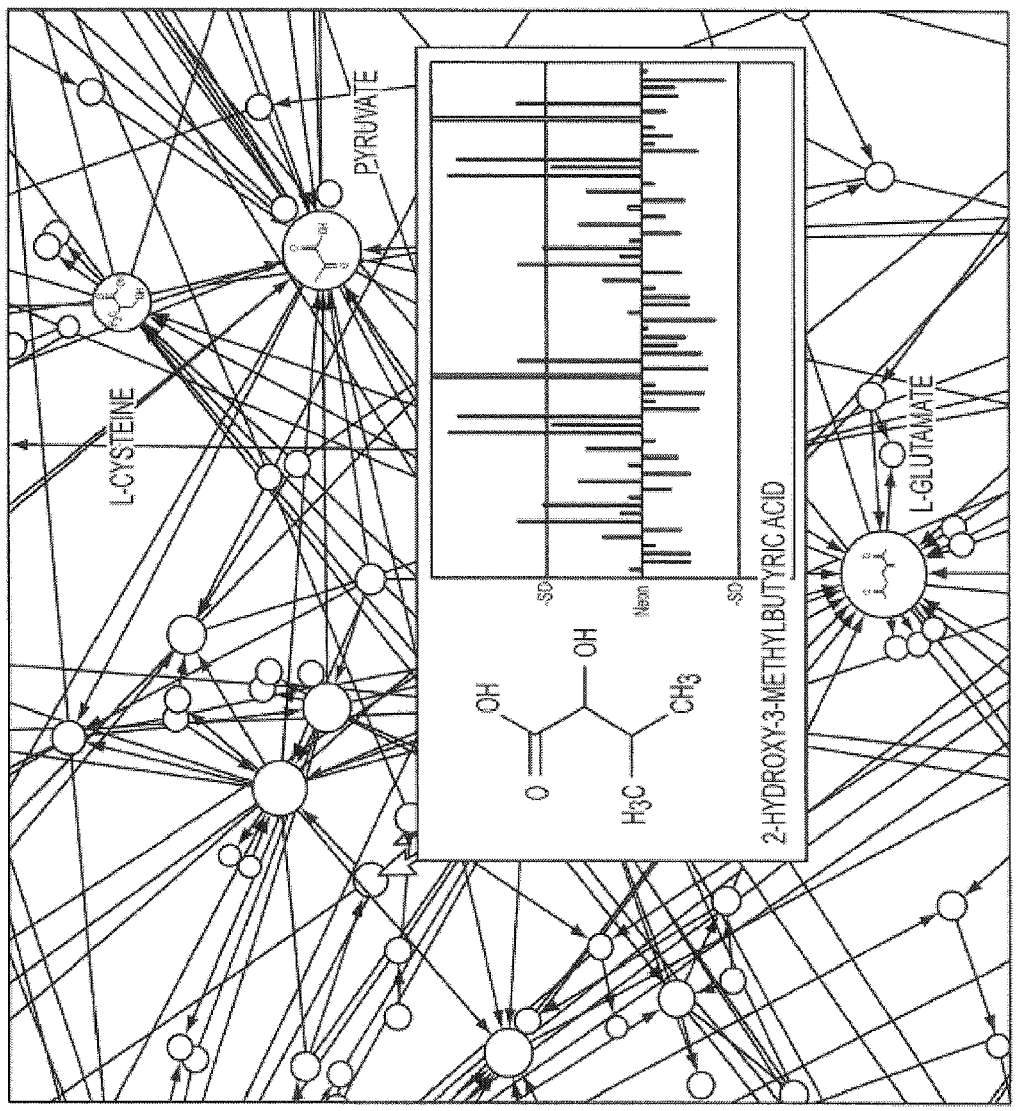
Figure 11:

In one example, 3-methyl-3-hydroxyglutarate (Internal ID=144) may have, in an enriched database, the following information associated with this particular metabolite: Chemspider ID=4573695 (FIG. 9A), KEGG ID=C03761 (FIG. 9B), and ChEMBL ID=17325 (FIG. 9C). Substantially instantaneously available, when queried, this information may be displayed on a graphic-user interface associated with the plugin according to the aspects, the systems, methods, and computer program products of the present disclosure (see FIG. 10). Active hyperlinks associated with the display may allow ready accessibility to external chemical/biological knowledge stored, for example, in Chemspider, ChEMBL and/or KEGG databases. Aspects of the aspects, the systems, methods, and computer program products of the present disclosure may also facilitate access, download, and visualization of large networks of chemical/biological pathways/relationships/associations, with additional functionality/features for highlighting particular features, wherein such functionality may include, for example, a standardized or extended color scheme and/or additional node/pathway annotation. For instance, graph indices may be available to characterize each network and quickly and readily identify hubs (i.e., nodes with a high vertex degree) or appropriate neighborhoods (e.g., metabolites that interact with at least two receptor proteins and another biological data type defined by a user) (FIG. 11). Aspects of the present disclosure may also provide the ability to browse and explore these networks using different user-friendly procedures and filters, using simple (e.g., metabolite identifiers) and complex (e.g., substructural similarity search) technologies, as appropriate. As such, users may, for example, be able to search across different pathways/relationships/associations for a particular metabolite based on any of its identifiers (see, e.g., FIG. 7A), or search for a set of metabolites based on chemical similarity to the user's query. In visualizing the results of such queries in a graphical format (i.e., displayed on a monitor or screen of a computer device), the users may not only view the actual results of the query, but may also view other nodes/relationships that are not included in the actual results but may be otherwise similar to, associated with, other otherwise relevant to the actual results (i.e., relevant information that may not have otherwise been seen from the actual results of the user query). Further, advanced data exploration tools such as, for example, analysis tools enabling enrichment analysis of cofactors via measurement of proximal metabolites, may also be included in some aspects of the present disclosure. Such advanced data exploration tools may, in some instances, be configured to apply statistical algorithms to the data in the context of the nodal network, wherein the results of such statistical procedures may be realized in association with the visually displayed results of the user query (i.e., such tools may, for example, statistically "rank" the relevant data related to the user query and present the relevant data, in response to the user query, in accordance with the relative statistical importance thereof).

In some instances, when metabolite profiles are available for a single, a group, or multiple groups (e.g., control vs. disease) of patients at different time points, aspects of the systems, methods, and computer program products of the present disclosure may allow the user to browse these profiles directly mapped on the pathway/relationship/association networks (see, e.g., FIG. 10) via dynamic frames that appear when a node is selected. In such instances, users may be directed to metabolite nodes that include the most significant profile variations for facilitating the analysis. Upon request, other types of information may be displayed in these dynamic frames, wherein such information may include, for example, public database ids, chemical structures, most similar metabolites, etc.

In another aspect of the present disclosure, a method 500 is provided (FIG. 12) for analyzing metabolomics data for a plurality of metabolites. A sample is analyzed to determine a first number of metabolites, and the amount of each metabolite, included in the sample, and a second number of metabolites, corresponding to an amount of the first number of metabolites included in the sample that are regulated metabolites (Block 520 and see, e.g., element 600 in FIG. 14). One or more biochemical pathways is determined, with each biochemical pathway having a third number of metabolites, corresponding to an amount of the first number of metabolites determined to be included in the sample and in the determined biochemical pathway (Block 540). For each of the determined biochemical pathways having the third number of metabolites, a fourth number of metabolites, corresponding to an amount of the second number of metabolites determined to be included in the sample and in the determined biochemical pathway that are regulated metabolites (Block 560). For one of the determined biochemical pathways, each of the third number of metabolites, is displayed (i.e., as a nodal network), wherein each metabolite is distinguished within the display by the amount of each corresponding metabolite determined to be included in the sample (Block 580 and see e.g., element 700 in FIGS. 14 and 15). In some instances, at least one of the nodes and/or one of the relationships therebetween may be annotated with empirical information associated therewith (i.e., from the analysis of the sample), previously known characterization data associated with a metabolite or a reaction (i.e., ontology classification data from a database), and/or relational information associated with other nodes and relationships.

In some instances, a category enrichment ratio may be determined for each of the determined biochemical pathways. The determined biochemical pathways may subsequently be ranked according to the determined category enrichment ratios, wherein the category enrichment ratio for a biochemical pathway indicates a significance of the metabolites determined to be included in the sample and in each of (or for a particular one of) the determined biochemical pathways. In one aspect, the ranked determined biochemical pathways may be displayed (e.g., on a computer monitor or display) as being distinguished from each other by a magnitude of the category enrichment ratio for each determined biochemical pathway (see, e.g., element 800 in FIGS. 14 and 16). For example, as shown in FIG. 16, the determined biochemical pathways may be distinguished according to rank by associating a color, a color gradation, or a font with an indicium of each of the determined biochemical pathways (see, e.g., elements 800A, 800B, and 800C in FIG. 16). In some instances, the displayed one of the determined biochemical pathways (i.e., nodal network) having metabolites determined to be included in the sample, wherein each metabolite is distinguished within the display by the amount of each corresponding metabolite determined to be included in the sample (Block 580 and see e.g., element 700 in FIGS. 14 and 15), may be selected according to the category enrichment ratio ranking thereof. That is, once the ranking of the biochemical pathways according to the category enrichment ratio is completed, one or more of the ranked biochemical pathways may be selected for further display (i.e., at element 700) from the ranking list of biochemical pathways shown at element 800.

In one aspect, the category enrichment ratio may be determined as or comprises a pathway enrichment ratio between a first quotient and a second quotient, wherein the first quotient is between the fourth number of the metabolites included in the sample and in the determined biochemical pathway that are regulated metabolites (i.e. number of regulated metabolites in the sample and in the determined biochemical pathway), and a total number of metabolites included in the determined biochemical pathway (i.e., number of metabolites in the determined biochemical pathway), and wherein the second quotient is between the second number of metabolites included in the sample that are regulated metabolites (i.e., total number of regulated metabolites in the sample), and the first number of metabolites (i.e., total number of metabolites in the sample) The inclusion of the category enrichment ratio in the data analysis may, for example, facilitate ranking of the biochemical pathways by enhancing distinctions related to the relative importance of the determined biochemical pathways, wherein such distinctions may otherwise not be readily discerned.

In regard to the display of the nodal network representing the selected one of the determined biochemical pathways, each metabolite in the sample may be represented as a node within the determined biochemical pathways. As such, each of the metabolites within the displayed one of the determined biochemical pathways and determined to be included in the sample (i.e., the third number of metabolites), is distinguished by the amount of each corresponding metabolite determined to be in the sample, for example, by varying a size, color, or color gradation of each node in the determined biochemical pathway in accordance with the amount (fold-change) of each corresponding metabolite determined to be included in the sample. Further, for each metabolite in the sample and included in the determined biochemical pathways (i.e., the third number of metabolites), each node may be annotated with actual data for the metabolite from analysis of the sample (i.e., empirical data), or previously known characterization data associated with the metabolite (i.e., ontology classification data from a database). The annotation associated with a node may be selectively displayed upon selection thereof on the displayed one of the determined biochemical pathways. For example, the annotations may appear by way of a "mouse-over" of the node or by way of a positive mouse click on that node.

In general, metabolomics data is comprised of the measured value (e.g., amount, concentration, relative level, fold change) obtained for each metabolite (biochemical) detected in the analysis of a sample. This empirical data obtained in the analysis for each metabolite or biochemical (i.e., metabolite data) in the sample may include a numerical value that represents the amount, (e.g., concentration or relative level) of the biochemical measured in the sample or the mean value for the amount of the biochemical in replicate samples, wherein the mean value may be associated with a standard deviation value. The metabolomics data may also comprise empirical data or information from one or more experiments, or from one or more comparisons, including statistical comparisons, and may be accompanied by a value representing a probability that the observed difference in relative quantification is statistically significant.

Each node in a biochemical pathway may be characterized by, associated with, or annotated with various attributes, including canonical biochemical pathway maps, classification areas of metabolism (e.g., biochemical super pathway, biochemical sub pathway), other ontologies (e.g., classification by disease, observation, clinical value, Medical Subject Heading (MeSH) terms, experimental treatment, chemical reaction, EC number, sample type, gene networks, Gene Ontology (GO) Consortium ontologies, genetic variants, signal transduction pathways, subcellular localization, etc.), reaction side, reactant type, name, IUPAC name, molecular formula, molecular weight, exact mass, structure, boiling point, melting point, density, database identifiers (e.g., SMILES, CAS, InChI, InChIKey, PubChem Identifier, HMDB Identifier, KEGG Identifier, Chemical Identifier, Enzyme Commission (EC) Number, Compound Identifier), Compound Type (e.g., fatty acid, amino acid, nucleotide, sugar, carbohydrate, organic acid, xenobiotic, etc.), relative level, amount or concentration, ratio data, Z-score, and statistical significance. The attributes can be fixed. Such fixed or known attributes may include canonical biochemical pathway maps, classification areas of metabolism (e.g., biochemical super pathway, biochemical sub pathway), certain ontologies, reaction side, reactant type, name, IUPAC name, molecular formula, molecular weight, exact mass, structure, boiling point, melting point, density, SMILES, CAS, InChI, InChIKey, PubChem Identifier, HMDB Identifier, KEGG Identifier, EC Number, Chemical Identifier, Compound Identifier, and Compound Type. The attributes can be variable. Such variable or empirical attributes include level, amount, or concentration, ratio data, Z-score, statistical significance, and certain ontologies. For example, in a biochemical pathway, a node may be a metabolite, and the amount of the metabolite/biochemical may differ according to a condition (e.g., disease) or an experimental treatment (e.g., drug dose) or study (e.g., case vs. control, treatment vs sham (placebo), time course), and the metabolite ratio data, Z-score, and statistical significance may vary depending on the comparison (e.g., case vs control, disease vs healthy, high dose vs. sham, early time points vs. later time points, etc.). Variable attributes may be empirical. The variable attributes may describe, for example, metabolites, genes, RNA transcripts, proteins. The proteins may be enzymes. In one example, metabolites and/or enzymes may be assigned to nodes, and the reaction side may be assigned to edges. In one aspect, each node may be annotated with one or more attributes. The attributes are associated with the node and are stored in a database. In some instances, one or more attributes may be uploaded to the database for each metabolite data set. In one example, nodes may be assigned one or more attributes related to metabolomics data and, optionally, may be assigned one or more attributes related to additional types of -omics data (e.g., genomics, transcriptomics, proteomics, DNA copy number, etc.).

In one aspect, according to aspects of the methods disclosed herein, each node may be assigned (whether automatically or at the direction of a user) one or more fixed attributes such as, for example, membership in one or more canonical biochemical pathway maps or membership in one or more classification areas of metabolism, and each node may also be associated with one or more variable attributes such as, for example, a measured amount and/or results data from one or more statistical comparisons.

In one aspect of the present disclosure, a method is provided for performing a metabolomics analysis of data for a plurality of metabolites within a sample, wherein such a method involves performing analytics on selected empirical (variable) attributes to rank order the biochemical pathways which involve metabolites found in the sample, thereby establishing a relative importance (ranking) and indicating an order in which an investigator should or could examine the experimental data by way of the biochemical pathways involving metabolites found in the sample. The attributes selected or associated with ranking the biochemical pathways can be a default selection setting or a user defined selection. The analysis may comprise generating an enrichment fold-change value (i.e., a score for the ontology based on the levels of metabolites within the ontology). In another example, aspects of such methods may be used or applied to rank order classification ontologies.

Aspects of the methods disclosed herein can be used to calculate or determine enrichment parameters for any designated classification/category, for example, to facilitate ranking of the biochemical pathways by enhancing distinctions related to the relative importance of the determined biochemical pathways, wherein such distinctions may otherwise not be readily discerned. In this regard, particular example(s) of the application of the method(s) are disclosed herein for the purposes of demonstration and clarification only, and are not intended to be limiting with respect to the applications thereof. As such, in one example, the disclosed method may be applied in performing analytics on metabolomics data obtained from analysis of a sample, using one or more selected attributes associated with the biochemical pathways and/or classification ontologies. The selected attributes may be a combination of one or more variable attributes and one or more fixed attributes. The empirical information/data may be used to perform analytics by first selecting the empirical information of interest (e.g., p-value), and second, by defining the attribute as regulated/responsive based on a threshold value (i.e., whether a metabolite or biochemical is a regulated metabolite or biochemical. The threshold value may be a user-defined threshold value for the one or more attributes comprising the empirical information, or may be a default threshold value for defining the one or more attributes as regulated/responsive (e.g., $p<0.05$). Subsequently, for each experiment or statistical comparison, a finite number, e, of biochemical/metabolites is denoted as responsive/regulated, out of the total number of biochemical/metabolites, E, detected (e.g., all biochemical/metabolites where $p \leq 0.05$ are considered responsive/regulated). Biochemical pathways are then similarly scored. That is, for each experiment or statistical comparison, a finite number, p, of biochemical/metabolites is noted as regulated, out of the total number of biochemical/metabolites, P, in the biochemical pathway that were detected. The Regulated Attribute Ratio (RAR or pathway enrichment ratio) is then calculated as the ratio of the quotient (p divided by P), versus the quotient (e divided by E). The RAR (pathway enrichment ratio) quantifies the number of regulated biochemical/metabolites in a specific biochemical pathway compared to the number of biochemical/metabolites in the studied sample, as a whole. RAR values (enrichment fold-change values) for each of the biochemical pathways in the experiment or statistical comparison are subsequently rank-ordered. The ordering of the biochemical pathways provides the investigator with the relative importance of the relevant biochemical pathways, allowing the investigator to prioritize examination of the biochemical/metabolites within those ranked pathways.

In another example, aspects of the methods disclosed herein can be used to provide a ranked order of pathway library reactions. In another example, the detected metabolites connected or related to or associated with a given reaction node may be placed in one category, and aspects of the method can be used to provide a ranked order of reaction nodes in the biochemical pathways.

For each experiment or statistical comparison (i.e., analysis of the sample), a threshold may be applied to a numerical quantification value and/or a statistical significance probability value. The threshold can be adjusted and is used to set the criterion value to determine if an attribute for each biochemical/metabolite is differentially present or "responsive" (e.g., increased or decreased, regulated or un-regulated) in the experiment or statistical comparison. In one example, a responsive biochemical attribute may be used to differentiate a case condition from a control condition. In another example, the case condition may be a disease sample(s) and the control condition may be a normal sample(s). In some instances, a biochemical attribute may be regulated or responsive, if differentially present as compared to a defined reference standard (e.g., a reference range, reference sample). The threshold can be dynamically manipulated by the investigator for each experiment or statistical comparison.

In one example, the attribute is the difference in the metabolite, RNA transcript, protein level (e.g., % change or fold-change) and the threshold may be set so that a biochemical, mRNA, or protein is considered regulated or responsive if differentially present at any level in the sample data, including a level that is increased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100%, by at least 110%, by at least 120%, by at least 130%, by at least 140%, by at least 150%, or more; or is generally present at a level that is decreased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, or by 100% (i.e., absent).

Statistical analysis may be used to determine if an attribute or biochemical may be considered regulated or responsive. For example, a biochemical/metabolite that is differentially present at a level that is statistically significant (e.g., a p-value less than 0.05), and/or a q-value of less than 0.10 as determined using a statistical test such as Welch's T-test or Wilcoxon's rank-sum Test with an adjustment for multiple comparisons such as Bonferoni or FDR), may be considered regulated or responsive. In another example, a biochemical/metabolite may be considered regulated or responsive, if differentially present with a Z-score of >1 or <−1, a Z-score of >1.5 or <−1.5, or a Z-score of >2.0 or <−2.0.

In regard to this analysis, it may be important to note that metabolites are not connected to other metabolites; rather, a biochemical pathway is drawn by connecting biochemical nodes to enzyme nodes representing proteins, genes or chemical reactions. Therefore, any edges represent a relationship between enzymes and metabolites, such as product or reactant, and not relationships between metabolites. Classification nodes, connected to enzyme nodes, may be used to represent classes of compounds (e.g. amino acids, long-chain fatty acids, etc.). A pop-up window may be used to display experimental data, relevant pathway ontologies, and/or a list of relevant pathway maps. Enzyme nodes may be annotated with Enzyme Commission (EC) numbers, while biochemical nodes may be annotated to internal identifiers. Metabolic Pathway maps may be connected to other metabolic pathway maps by connecting metabolite nodes to nodes representing metabolic pathway maps. Mouse clicking a pathway map node may serve to open that pathway map. Sub Pathway ontology nodes and Pathway Map nodes may be overlaid with enrichment fold change values. In addition, toggling capability may be provided in regard to the display of selected experiments and statistical comparisons, or map rendering of nodes by compound type (e.g. cofactors, minor metabolites).

According to aspects of the methods disclosed herein, metabolite profiles for an individual, a group of individuals, or multiple groups of individuals may be visualized by display based on ontologies. Statistical data (e.g., Z-score, t-tests) may be uploaded through the integration of software, for example, a LIMS. In one example, metabolomics data from an individual patient sample was stored in the described data analysis tool, and statistical Z-score data for the patient sample was uploaded through integration with mLIMS. Within the data analysis tool, each metabolite is assigned to one or more biochemical pathway ontologies. A query was performed on the metabolomics data for visualization of the biochemical pathway ontologies. The twelve biochemical pathways that met the criteria of the user query are displayed in FIG. 15. Enrichment values were determined for the biochemical pathways based on parameters selected in the query. For biochemical pathways, enrichment is calculated based on the number of significant metabolites in the pathway, the number of detected metabolites in the pathway, the total number of significant metabolites, and the total number of detected metabolites. As shown in FIG. 15, the fold enrichment (e.g., change in amount) for each biochemical pathway classification is plotted along the x-axis. Significant classifications may be colored, with the gradient level of color representative of fold enrichment (e.g., yellow to orange to red). The statistical significance of the enrichment for each biochemical pathway was determined, and the significance is indicated by p-values; statistically significant pathways are denoted with p-values in bold italics. In this instance, based on the enrichment results of the user query, the branched chain amino acid (BCAA) metabolism biochemical pathway was displayed, as shown in FIG. 14. FIG. 14 illustrates the BCAA metabolism biochemical pathway display of the metabolomics data from the patient sample. In FIG. 14, rectangles represent enzymes, circles represent significant metabolites, arrows represent reactions in the biochemical pathway, and filled circles represent metabolites detected in this patient sample. The size of the circle represents the magnitude of the measured change (i.e., fold-change) of the metabolite level relative to the reference level (i.e., the larger the circle, the larger the measured difference in metabolite level compared to the reference level). Multiple panels may be viewed in visual proximity as shown in FIG. 13.

In yet another aspect of the present disclosure, a computer program product is provided comprising at least one non-transitory computer readable storage medium having computer program code stored thereon. The program code of this embodiment may include program code for at least performing the steps of the method aspect upon execution thereof. That is, it will be understood that each block of the flowchart in FIG. 1, and/or combinations of blocks in the flowchart, may be implemented by various means, such as hardware and/or a computer program product comprising one or more computer-readable mediums having computer readable program instructions stored thereon. For example, one or more of the procedures described herein may be embodied by computer program instructions of a computer program product. In this regard, the computer program product(s), which may embody the procedures described herein, may be stored by one or more memory devices of a mobile terminal, server, or other suitable computing device and executed by a processor in the computing device. In some embodiments, the computer program instructions comprising the computer program product(s) which embody the procedures described above may be stored by memory devices of a plurality of computing devices. As will be appreciated, any such computer program product may be loaded onto a computer or other programmable apparatus to produce a machine, such that the computer program product including the instructions which execute on the computer or other programmable apparatus creates means for implementing the functions specified in the flowchart block(s). Further, the computer program product may comprise one or more computer-readable memories on which the computer program instructions may be stored such that the one or more computer-readable memories can direct a computer or other programmable apparatus to function in a particular manner, such that the computer program product comprises an article of manufacture which implements the function specified in the flowchart block(s). The computer program instructions of one or more computer program products may also be loaded onto a computer or other programmable apparatus to cause a series of operations to be performed on the computer or other programmable apparatus to produce a computer-implemented process such that the instructions which execute on the computer or other programmable apparatus implement the functions specified in the flowchart block(s). Accordingly, blocks of the flowchart support combinations of means for performing the specified functions. It will also be understood that one or more blocks of the flowchart, and combinations of blocks in the flowchart, may be implemented by special purpose hardware-based computer systems which perform the specified functions, or combinations of special purpose hardware and computer program product(s).

In yet another aspect of the present disclosure, an apparatus comprising processing circuitry, or at least an appropriate processor, is provided. The processing circuitry of this example embodiment may be configured to control the apparatus to at least perform the steps of the method aspect. In this regard, FIG. 12 illustrates a block diagram of an apparatus 300 that can be implemented on a server in accordance with some example embodiments. In this regard, when implemented on a computing device, such as a server, apparatus 300 can enable a computing device to operate within a system in accordance with one or more example embodiments. It will be appreciated that the components, devices or elements illustrated in and described with respect to FIG. 12 below may not be mandatory and thus some may be omitted in certain embodiments. Additionally, some embodiments can include further or different components, devices or elements beyond those illustrated in and described with respect to FIG. 12.

In some example embodiments, the apparatus 300 can include processing circuitry 310 that is configurable to perform actions in accordance with one or more example embodiments disclosed herein, such as method aspects previously disclosed. In this regard, the processing circuitry 310 can be configured to perform and/or control performance of one or more functionalities of the apparatus 300 in accordance with various example embodiments, and thus can provide means for performing functionalities of the apparatus 300 in accordance with various example embodiments. The processing circuitry 310 can be configured to perform data processing, application/software execution and/or other processing and management services according to one or more example embodiments.

In some embodiments, the apparatus 300 or a portion(s) or component(s) thereof, such as the processing circuitry 310, can include one or more chipsets, which can each include one or more chips. The processing circuitry 310 and/or one or more further components of the apparatus 300 can therefore, in some instances, be configured to implement an embodiment on a single chip or chipset. In some example embodiments in which one or more components of the apparatus 300 are embodied as a chipset, the chipset can be capable of enabling a computing device to operate in the system 200 when implemented on or otherwise operably coupled to the computing device. Thus, for example, one or more components of the apparatus 300 can provide a chipset configured to enable a computing device to operate over a network.

In some example embodiments, the processing circuitry 310 can include a processor 312 and, in some embodiments, such as that illustrated in FIG. 12, can further include a memory 314. The processing circuitry 310 can be in communication with or otherwise control a communication interface(s) 316 and/or selection control module 318, as further disclosed herein.

The processor 312 can be embodied in a variety of forms, as will be appreciated by one of ordinary skill in the art. For example, the processor 312 can be embodied as various processing means such as a microprocessor, a coprocessor, a controller or various other computing or processing devices including integrated circuits such as, for example, an application-specific integrated circuit (ASIC), a field-programmable gate array (FPGA), some combination thereof, or the like. Although illustrated as a single processor, it will be appreciated that the processor 312 can comprise a plurality of processors. The plurality of processors can be in operative communication with each other and can be collectively configured to perform one or more functionalities of the apparatus 300 as described herein. In some example embodiments, the processor 312 can be configured to execute instructions that can be stored in the memory 314 or that can be otherwise accessible to the processor 312. As such, whether configured by hardware or by a combination of hardware and software, the processor 312 is capable of performing operations according to various embodiments while configured accordingly.

In some example embodiments, the memory 314 can include one or more memory devices. The memory 314 can include fixed and/or removable memory devices. In some embodiments, the memory 314 can provide a non-transitory computer-readable storage medium that can store computer program instructions (i.e., software) that can be executed by the processor 312. In this regard, the memory 314 can be configured to store information, data, applications, instructions and/or the like for enabling the apparatus 300 to carry out various functions in accordance with one or more example embodiments, such as the method aspects disclosed herein. In some embodiments, the memory 314 can be in communication with one or more of the processor 312, communication interface(s) 316, or selection control module 318 via a bus(es) for passing information among components of the apparatus 300.

The apparatus 300 may further include a communication interface 316. The communication interface 316 may enable the apparatus 300 to receive a signal that may be sent by another computing device, such as over a network. In this regard, the communication interface 316 may include one or more interface mechanisms for enabling communication with other devices and/or networks. As such, the communication interface 316 may include, for example, an antenna (or multiple antennas) and supporting hardware and/or software for enabling communications with a wireless communication network (e.g., a cellular network, WLAN, and/or the like) and/or a communication modem or other hardware/software for supporting communication via cable, digital subscriber line (DSL), USB, FireWire, Ethernet or other wireline networking methods.

The apparatus 300 can further include selection control module 318. The selection control module 318 can be embodied as various means, such as circuitry, hardware, a computer program product comprising a computer readable medium (for example, the memory 314) storing computer readable program instructions and executable by a processing device (for example, the processor 312), or some combination thereof for performing particular operations or functions of aspects of the present disclosure, as otherwise disclosed herein. In some embodiments, the processor 312

(or the processing circuitry 310) can include, or otherwise control the selection control module 318.

Many modifications and other embodiments of the inventions set forth herein will come to mind to one skilled in the art to which these inventions pertain having the benefit of the teachings presented in the foregoing descriptions and the associated drawings. For example, the apparatus, methods, and computer program products disclosed herein may be adapted to integrate up to 4 or more -omics data types (e.g. metabolomics, RNA-seq, microarray, proteomics, miRNA-seq, etc.) by coloring enzyme nodes directly within a biochemical pathway, to enable user to examine relationships between the various -omics data types and between biological experiments. Relative activity may be indicated by rank-ordering metabolic pathway maps using an enrichment fold change calculation, and bipartite networks connecting a node representing an experiment or statistical comparison to nodes representing either (1) biochemicals, (2) metabolic pathway maps, (3) pathway ontologies, or (4) keyword ontologies, may be generated. A pathway classification network may also be generated, with such a network comprising nodes representing a Super Pathway ontology, connected to nodes representing Sub Pathway Ontologies, connected to nodes representing the biochemical/metabolite members of the Sub Pathway Ontology.

Therefore, it is to be understood that the embodiments of the invention are not to be limited to the specific embodiments disclosed and that modifications and other embodiments are intended to be included within the scope of the invention. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the invention. In this regard, for example, different combinations of elements and/or functions than those explicitly described above are also contemplated within the scope of the invention. Although specific terms are employed herein, they are used in a generic and descriptive sense only and not for purposes of limitation.

That which is claimed:

1. A method of analyzing metabolomics data for a sample to detect a plurality of metabolites in the sample, comprising:
    inputting into a user interface one or more selected attributes associated with the sample;
    analyzing the metabolomics data based on the one or more selected attributes to detect a first number of metabolites, and the amount of each metabolite, present in the sample;
    detecting a second number of metabolites, corresponding to one or more regulated metabolites present in the first number of metabolites;
    detecting a third number of metabolites present in the first number of metabolites and present in each of one or more biochemical pathways associated with the sample;
    for each of the one or more biochemical pathways having the third number of metabolites, detecting a fourth number of metabolites, corresponding to regulated metabolites present in the sample and in the respective biochemical pathway;
    diagnosing a significance of the third number of metabolites in each of the one or more biochemical pathways, as indicated by a category enrichment ratio associated therewith, by:
        distinguishing each of the third number of metabolites within one of the one or more biochemical pathways, on a display, by the amount of each corresponding metabolite detected in the sample;
        determining a category enrichment ratio for each of the one or more biochemical pathways, by determining a pathway enrichment ratio between a first quotient and a second quotient, the first quotient being between the fourth number of the metabolites and a total number of metabolites included in the respective biochemical pathway, and the second quotient being between the second number of metabolites and the first number of metabolites in the sample;
        ranking the one or more biochemical pathways by their category enrichment ratio;
        displaying an indicium of each of the one or more ranked biochemical pathways on the display such that the indicia of the ranked one or more biochemical pathways are distinguished from each other;
    allowing the user to vary the one or more selected attributes inputted into the user interface;
    automatically re-ranking the one or more biochemical pathways in response to the varying of the one or more selected attributes by the user; and
    displaying a new distinguishing indicium of each of the one or more re-ranked biochemical pathways.

2. The method of claim 1, wherein each displayed indicium represents a magnitude of the category enrichment ratio for each biochemical pathway.

3. The method of claim 2, wherein the indicia are distinguished by a color, a color gradation, or a font.

4. The method of claim 1, wherein distinguishing each of the third number of metabolites within the one of the one or more biochemical pathways comprises distinguishing each of the third number of metabolites within the one of the one or more biochemical pathways according to the ranking of the category enrichment ratio thereof.

5. The method of claim 1, wherein each metabolite in the sample is represented as a node within the one or more biochemical pathways, and distinguishing each of the third number of metabolites within the one of the one or more biochemical pathways by the amount of each corresponding metabolite detected in the sample further comprises distinguishing the metabolites in the sample by varying a size, color, or color gradation of each node in the one of the one or more biochemical pathways displayed on the display in accordance with the amount of each corresponding metabolite detected in the sample.

6. The method of claim 5, further comprising annotating each node with actual data for the metabolite from the analysis of the sample, or previously known characterization data associated with the metabolite.

7. The method of claim 6, further comprising displaying the annotation associated with the node upon selection thereof on the displayed one of the one or more biochemical pathways.

8. An apparatus for analyzing metabolomics data for a sample to detect a plurality of metabolites in the sample, comprising:
    a processor configured to control a device to at least:
        analyze the metabolomics data based on one or more selected attributes to detect a first number of metabolites, and the amount of each metabolite, present in the sample;
        detect a second number of metabolites, corresponding to one or more regulated metabolites present in the first number of metabolites;

detect a third number of metabolites present in the first number of metabolites and present in each of one or more biochemical pathways associated with the sample;

for each of the one or more biochemical pathways having the third number of metabolites, detect a fourth number of metabolites, corresponding to regulated metabolites present in the sample and in the respective biochemical pathway; and diagnose a significance of the third number of metabolites in each of the one or more biochemical pathways, as indicated by a category enrichment ratio associated therewith, by:

distinguishing each of the third number of metabolites within one of the one or more biochemical pathways, on a display, according to the amount of each corresponding metabolite detected in the sample;

determining a category enrichment ratio for each of the one or more biochemical pathways, by determining a pathway enrichment ratio between a first quotient and a second quotient, the first quotient being between the fourth number of the metabolites and a total number of metabolites included in the respective biochemical pathway, and the second quotient being between the second number of metabolites and the first number of metabolites in the sample;

ranking the one or more biochemical pathways by their category enrichment ratio;

displaying an indicium of each of the one or more biochemical pathways on the display such that the indicia of the ranked one or more biochemical pathways are distinguished from each other; and a user interface in communication with the processor and configured to have inputted therein the one or more selected attributes associated with the sample, the user interface being further configured to allow the user to vary the one or more selected attributes inputted into the user interface, and in response to the varying of the one or more selected attributes by the user, cause the processor to automatically re-rank the one or more biochemical pathways, and display a new distinguishing indicium of each of the one or more re-ranked biochemical pathways.

9. The apparatus of claim 8, wherein the processor is further configured to control the device such that each displayed indicium represents a magnitude of the category enrichment ratio for each biochemical pathway.

10. The apparatus of claim 9, wherein the processor is further configured associate a color, a color gradation, or a font with an indicium of each of the biochemical pathways.

11. The apparatus of claim 8, wherein the processor is configured to control the device to distinguish each of the third number of metabolites within the one of the one or more biochemical pathways according to the ranking of the category enrichment ratio thereof.

12. The apparatus of claim 8, wherein each metabolite in the sample is represented as a node within the one or more biochemical pathways, and wherein the processor is further configured to control the device to distinguish the metabolites in the sample by varying a size, color, or color gradation of each node in the one of the one or more biochemical pathways displayed on the display in accordance with the amount of each corresponding metabolite detected in the sample.

13. The apparatus of claim 12, wherein the processor is further configured to control the device to annotate each node with actual data for the metabolite from the analysis of the sample, or previously known characterization data associated with the metabolite.

14. The apparatus of claim 13, wherein the processor is further configured to control the device to display the annotation associated with the node upon selection thereof on the displayed one of the one or more biochemical pathways.

15. A computer program product comprising at least one non-transitory computer readable storage medium having computer program code stored thereon, the computer program code being configured to analyze metabolomics data for a sample to detect a plurality of metabolites in the sample, and comprising:

program code for receiving one or more selected attributes associated with the sample inputted into a user interface;

program code for analyzing the metabolomics data based on the one or more selected attributes to detect a first number of metabolites, and the amount of each metabolite, present in the sample;

program code for detecting a second number of metabolites, corresponding to one or more regulated metabolites present in the first number of metabolites;

program code for detecting a third number of metabolites present in the first number of metabolites and present in each of one or more biochemical pathways associated with the sample;

program code for detecting, for each of the one or more biochemical pathways having the third number of metabolites, a fourth number of metabolites, corresponding to regulated metabolites present in the sample and in the respective biochemical pathway;

program code for diagnosing a significance of the third number of metabolites in each of the one or more biochemical pathways, as indicated by a category enrichment ratio associated therewith, by:

distinguishing each of the third number of metabolites within one of the one or more biochemical pathways, on a display, according to the amount of each corresponding metabolite detected in the sample;

determining a category enrichment ratio for each of the one or more biochemical pathways, by determining a pathway enrichment ratio between a first quotient and a second quotient, the first quotient being between the fourth number of the metabolites and a total number of metabolites included in the respective biochemical pathway, and the second quotient being between the second number of metabolites and the first number of metabolites in the sample; and ranking the one or more biochemical pathways by their category enrichment ratio;

displaying an indicium of each of the one or more ranked biochemical pathways on the display such that the indicia of the ranked one or more biochemical pathways are distinguished from each other; and program code for allowing the user to vary the one or more selected attributes inputted into the user interface;

program code for automatically re-ranking the one or more biochemical pathways in response to the varying of the one or more selected attributes by the user program code for displaying a new distinguishing indicium of each of the one or more re-ranked biochemical pathways.

16. The computer program product of claim 15, wherein each displayed indicium represents a magnitude of the category enrichment ratio for each biochemical pathway.

17. The computer program product of claim 16, wherein the program code further associates a color, a color gradation, or a font with an indicium of each of the biochemical pathways.

18. The computer program product of claim 15, wherein the program code for distinguishing each of the third number of metabolites within the one of the one or more biochemical pathways comprises program code for distinguishing each of the third number of metabolites within the one of the one or more biochemical pathways according to the ranking of the category enrichment ratio thereof.

19. The computer program product of claim 15, wherein each metabolite in the sample is represented as a node within the one or more biochemical pathways, and wherein the program code for distinguishing each of the third number of metabolites within one of the one or more biochemical pathways by the amount of each corresponding metabolite detected in the sample, further comprises program code for distinguishing the metabolites in the sample by varying a size, color, or color gradation of each node in the one of the one or more biochemical pathways displayed on the display in accordance with the amount of each corresponding metabolite detected in the sample.

20. The computer program product of claim 19, further comprising program code for annotating each node with actual data for the metabolite from the analysis of the sample, or previously known characterization data associated with the metabolite.

21. The computer program product of claim 20, further comprising program code for displaying the annotation associated with the node upon selection thereof on the displayed one of the one or more biochemical pathways.

* * * * *